(12) United States Patent
Rademacher et al.

(10) Patent No.: US 8,568,781 B2
(45) Date of Patent: Oct. 29, 2013

(54) PEPTIDE-CARRYING NANOPARTICLES

(75) Inventors: Thomas Rademacher, Oxfordshire (GB); Phillip Williams, Oxfordshire (GB); Christof Bachmann, Oxfordshire (GB); Africa Garcia Barrientos, Bizkaia (ES); Esther de Torres Dominguez, Elgoibar-Guipuzkoa (ES); Javier del Campo Menoyo, Bilbao-Bizkaia (ES)

(73) Assignee: Midatech Limited, Abingdon, Oxford (GB)

( * ) Notice: Subject to any disclaimer, the term of this patent is extended or adjusted under 35 U.S.C. 154(b) by 0 days.

(21) Appl. No.: 13/157,783

(22) Filed: Jun. 10, 2011

(65) Prior Publication Data

US 2012/0171291 A1  Jul. 5, 2012

Related U.S. Application Data

(60) Provisional application No. 61/353,380, filed on Jun. 10, 2010.

(51) Int. Cl.
| A61K 9/14 | (2006.01) |
| A61K 38/00 | (2006.01) |
| A61K 38/28 | (2006.01) |
| C07K 5/00 | (2006.01) |
| C07K 7/00 | (2006.01) |

(52) U.S. Cl.
USPC .............. 424/489; 514/1.1; 514/6.8; 514/6.9; 530/303; 530/304; 530/308; 977/773; 977/795; 977/838; 977/906

(58) Field of Classification Search
USPC ............ 424/489, 490; 514/1.2, 11.7, 5.9, 6.8, 514/6.9, 1.1; 530/303, 304, 308, 906; 977/773, 795, 838, 906; 536/17.1
See application file for complete search history.

(56) References Cited

U.S. PATENT DOCUMENTS 8,425,915 B2 *  4/2013  Rademacher et al. ..... 424/194.1

FOREIGN PATENT DOCUMENTS

| EP | 2 305 310 A1 | 4/2011 |
| WO | 02/32404 A2 | 4/2001 |
| WO | WO 02/32404 A2 * | 4/2002 |
| WO | 2004/108165 A2 | 12/2004 |
| WO | WO 2004/108165 A2 * | 12/2004 |
| WO | 2005116226 A2 | 5/2005 |
| WO | 2005091704 A2 | 10/2005 |
| WO | 2006037979 A2 | 4/2006 |
| WO | WO 2006/037979 A2 * | 4/2006 |
| WO | 2007015105 A2 | 2/2007 |
| WO | WO 2007/015105 A2 * | 2/2007 |

(Continued)

OTHER PUBLICATIONS

Whiteley et al. ("Helper T-cell clones that recognize autologous insulin are stimulated in nonresponder mice by pork insulin" in Proc. Natl. Acad. Sci. USA., vol. 85, pp. 2723-2727, Apr. 1988(Immunology).*

(Continued)

*Primary Examiner* — Blessing M Fubara
(74) *Attorney, Agent, or Firm* — Patrick J. Hagan; Dann, Dorfman, Herrell and Skillman, P.C.

(57) ABSTRACT

Nanoparticles having a core and a corona of ligands covalently linked to the core, wherein peptides are bound to or associated with the nanoparticles.

95 Claims, 19 Drawing Sheets

(56) References Cited

FOREIGN PATENT DOCUMENTS

| WO | 2007122388 A2 | 11/2007 |
| WO | WO 2009/136763 A2 * | 11/2009 |
| WO | WO 2010/052503 A1 * | 5/2010 |

OTHER PUBLICATIONS

Hrushikesh et al., ("Gold Nanoparticles as Carriers for Efficient Transmucosal Insulin Delivery" in Langmuir, 2006, 22(1), pp. 300-305).*

* cited by examiner

US 8,568,781 B2

PEPTIDE-CARRYING NANOPARTICLES

CROSS-REFERENCE TO RELATED APPLICATIONS

The present application claims the benefit of U.S. Provisional Patent Application No. 61/353,380, filed Jun. 10, 2010, filed Jan. 19, 2007, the entire disclosure of which is incorporated by reference herein.

FIELD OF THE INVENTION

The present invention relates to peptide-carrying nanoparticles, particularly for use in medicine, and includes methods for treatment of disorders, e.g., of blood glucose regulation.

BACKGROUND TO THE INVENTION

The present invention is directed at compositions and products, and methods of making and administering such compositions and products, including for the treatment of mammals and particularly humans.

Bioactive agents, such as peptides, frequently suffer from poor stability, particularly thermo-stability, which may limit the conditions to which the agents can be subjected during preparation, processing, storage and/or delivery. For example, insulin is widely-used in the control and treatment of, e.g., Type 1 & Type 2 diabetes mellitus. Medical preparations of insulin for human use are generally formulated with one or more preservatives and/or stabilisers. Moreover, limited gastrointestinal stability typically presents a barrier to effective oral administration of bioactive peptides, such as insulin.

There remains an unmet need for compositions capable of carrying and/or stabilising bioactive peptides, including insulin, and for methods of delivering such bioactive peptides to a subject.

BRIEF DESCRIPTION OF THE INVENTION

The present invention addresses the aforementioned difficulties by providing a suitable active-carrying component for stabilisation and delivery of active agents such as peptides, i.e., a component which is linked to, bound to, associated with or otherwise coupled to an active.

The present invention provides nanoparticles which as described herein, include a metal core, a corona of ligands and an active bound to one or more of the ligands. In this way, the nanoparticles of the present invention provide a carrier or delivery component for bioactive peptides, such as insulin, which peptides may thereby be stabilised.

In one aspect of the invention, there is provided a nanoparticle comprising:

(i) a core which includes a metal; and
(ii) a corona including a plurality of ligands covalently linked to the core, wherein at least one of said ligands includes a carbohydrate moiety; and
(iii) wherein at least one peptide is non-covalently bound to the corona. The peptide may, in some cases, be reversibly and/or non-covalently bound to the corona.

The peptide may be bound to the corona such that at least a fraction, or more, of the bound peptide is released from the nanoparticle upon contacting the nanoparticle with a physiological solution, e.g. a saline solution. The release may facilitate biological effects of an active peptide, for example by allowing the peptide to interact with its receptor. Generally, the peptide will be a bioactive peptide, i.e. capable of stimulating a physiological response in a mammalian subject. In some cases in accordance with the present invention the peptide may be selected from the group consisting of: insulin, GLP-1, IGF1, IGF2, relaxin, INSL5, INSL6, INSL7, pancreatic polypeptide(PP), peptide tyrosine tyrosine (PTT), neuropeptide Y, oxytocin, vasopressin, GnRH, TRH, CRH, GHRH/somatostatin, FSH, LH, TSH, CGA, prolactin, ClIP, ACTH, MSH, enorphins, lipotropin, GH, calcitonin, PTH, inhibin, relaxin, hCG, HPL, glucagons, insulin, somatostatin, melatonin, thymosin, thmulin, gastrin, ghrelin, thymopoietin, CCK, GIP secretin, motin VIP, enteroglucagon, IGF-1, IGF-2, leptin, adiponectin, resistin Osteocalcin, renin, EPO, calicitrol, ANP, BNP, chemokines, cytokines, adipokines and all biologically active analogues thereof. Thus, in certain cases the peptide may be capable of stimulating a reduction in blood glucose levels in a mammalian subject. For example, the peptide may comprise or consist of monomeric and/or dimeric human insulin. Furthermore, the peptide may comprise or consist of GLP-1 or an analogue thereof. Furthermore, the at least one peptide may comprise a combination of two or more peptides specified above, e.g. insulin and GLP-1, or insulin and a GLP-1 analogue.

In some cases in accordance with the present invention said carbohydrate moiety may comprises a monosaccharide and/or a disaccharide. The carbohydrate moiety may be as defined further herein, including a carbohydrate mimetic. The carbohydrate moiety may be covalently linked to the core via a linker selected from the group consisting of: sulphur-containing linkers, amino-containing linkers, phosphate-containing linkers and oxygen-containing linkers. In some cases the linker comprises an alkyl chain of at least two carbons.

In accordance with the present invention said at least one ligand comprising a carbohydrate moiety may in some cases be selected from the group consisting of: 2'-thioethyl-α-D-galactopyranoside, 2'-thioethyl-β-D-glucopyranoside, 2'-thioethyl-2-acetamido-2-deoxy-β-D-glucopyranoside, 5'-thiopentanyl-2-deoxy-2-imidazolacetamido-α,β-D-glucopyranoside and 2'-thioethyl-α-D-glucopyranoside, wherein said at least one ligand comprising a carbohydrate moiety is covalently linked to the core via its sulphur atom.

It is specifically contemplated herein that said plurality of ligands covalently linked to the core may comprise at least a first ligand and a second ligand, wherein the first and second ligands are different. For example the first and second ligands may be as follows:

(a) said first ligand comprises 2'-thioethyl-α-D-galactopyranoside and said second ligand comprises 1-amino-17-mercapto-3,6,9,12,15,-pentaoxa-heptadecanol;
(b) said first ligand comprises 2'-thioethyl-β-D-glucopyranoside or 2'-thioethyl-α-D-glucopyranoside and said second ligand comprises 5'-thiopentanyl-2-deoxy-2-imidazolacetamido-α,β-D-glucopyranoside;
(c) said first ligand comprises 2'-thioethyl-β-D-glucopyranoside or 2'-thioethyl-α-D-glucopyranoside and said second ligand comprises 1-amino-17-mercapto-3,6,9,12,15,-pentaoxa-heptadecanol; or
(d) said first ligand comprises 2'-thioethyl-2-acetamido-2-deoxy-β-D-glucopyranoside and said second ligand comprises 1-amino-17-mercapto-3,6,9,12,15,-pentaoxa-heptadecanol, and wherein said first and second ligands are covalently linked to the core via their respective sulphur atoms.

In some cases the first ligand may comprise a carbohydrate moiety and said second ligand a non-carbohydrate ligand. One or more of the ligands may an amine group. In particular, the second ligand may comprise 1-amino-17-mercapto-3,6,
9,12,15,-pentaoxa-heptadecanol covalently linked to the core
via its sulphur atom.

As described further herein, where there different ligands
are present on the nanoparticle they may be present at, e.g.,
certain defined ratios or ranges of ratios. For example, the first
ligand and said second ligand may present on the nanoparticle
in a ratio in the range of 1:40 to 40:1, 1:10 to 10:1 or even 1:2
to 2:1.

It has been found that the nanoparticles in accordance with
the present invention may be provided with a variety of numbers of ligands forming the corona. For example, in some
cases the corona comprises at least 5 ligands per core, e.g.
between about 10 to about 1000 ligands per core or 44-106
ligands per core.

The number of peptide molecules bound per core is not
particularly limited. For certain applications, it may be desirable to employ as few as 1, 2, 3 or 4 peptides per core, while
in other cases the nanoparticle of the invention may comprise
at least 5 or more peptide molecules bound per core.

In accordance with the present invention, the nanoparticle
core may in some cases comprise a metal selected from the
group consisting of: Au, Ag, Cu, Pt, Pd, Fe, Co, Cd, Gd, Zn or
any combination thereof. Certain metal combinations and
particular core compositions are described further herein.

The nanoparticle core in accordance with the present
invention may in some cases have a diameter in the range of
about 0.5 nm to about 50 nm, such as about 1 nm to about 10
nm or about 1.5 nm to about 2 nm.

In accordance with the present invention said at least one
peptide may comprise at least two, three, four, five or more
different species of peptide. In particular, the nanoparticle
may comprise insulin and GLP-1 bound to the corona of the
same nanoparticle. The presence of more than one species of
peptide bound to the nanoparticle may be preferred in certain
settings (e.g. certain clinical settings) as compared with binding of a single species of peptide. In particular, combinations
of peptides may be carried on a nanoparticle such that the
peptides perform mutually beneficial or complementary
functions and/or act in concert, such as in a synergistic fashion. The presence of more than one species may be used for
the purpose of treating one or more conditions and for one or
more therapeutic indications.

In accordance with the present invention the nanoparticle
of the invention may comprise a component having a divalent
state, such as a metal or a compound having a divalent state,
or an oxide or salt thereof. For example, metals or metal
complexes having the ability to exist in a divalent state are
particularly useful. Such a component may be in the divalent
state as added or may be transformed into a divalent state after
addition. Oxides and salts of the divalent component are also
useful and may be added directly or formed in situ subsequent
to addition. Among the useful salts of the divalent component
include halide salts, such as chloride, iodide, bromide and
fluoride. Such divalent components may include, for
example, zinc, magnesium, copper, nickel, cobalt, cadmium,
or calcium, and their oxides and salts thereof. The component
is desirably present in an amount sufficient to produce a
stabilizing effect and/or in an amount sufficient to enhance
the binding of the peptide to the corona to t level great than the
level of binding of the peptide to the corona in the absence of
the component having a divalent state. In some cases, the
component having a divalent state is desirably present in an
amount of about 0.5 to 2.0 equivalents to the core metal (e.g.
gold), or optionally about 0.75 to 1.5 equivalents to the core
metal (e.g. gold). In the context of the present invention,
"equivalents" may be mole equivalents, for example 1.0
equivalent of zinc may be taken to mean the same number of
zinc atoms or $Zn^{2+}$ cations as the number of gold atoms in the
core of the nanoparticle.

The divalent component may in some cases be present in
the corona of the nanoparticle. It is specifically contemplated
herein that the divalent component may be included in the
nanoparticle, including in the corona of the nanoparticle as a
result of inclusion of the divalent component in the process of
synthesis of the nanoparticle. Additionally or alternatively,
the divalent component may be added after synthesis of the
nanoparticle. In some cases in accordance with the present
invention, the divalent component, such as zinc may be
selected from: $Zn^{2+}$ and ZnO. For example, the zinc may be in
the form of $ZnCl_2$.

In a further aspect the invention provides a plurality of
nanoparticles of the invention. For example, a plurality may
be 100, 1000, 100000, or more. The plurality may be in as
associated form, a suspension or contained together in a
single package, container or carrier. In certain cases, the
plurality may take the form of one or more doses (e.g. a
defined quantity of peptide or peptide activity units), such as
in the form of a therapeutic dose or defined number of doses.

In a further aspect the present invention provides a nanoparticle comprising:
 (i) a core comprising a metal;
 (ii) a corona comprising a plurality of ligands covalently
    linked to the core, which plurality of ligands comprises
    at least a first ligand and a second ligand, wherein:
  (a) said first ligand comprises 2'-thioethyl-α-D-galactopyranoside and said second ligand comprises 1-amino-17-mercapto-3,6,9,12,15,-pentaoxa-heptadecanol;
  (b) said first ligand comprises 2'-thioethyl-β-D-glucopyranoside or 2'-thioethyl-α-D-glucopyranoside and said second ligand comprises 5"-thiopentanyl-2-deoxy-2-imidazolacetamido-α,β-D-glucopyranoside;
  (c) said first ligand comprises 2'-thioethyl-β-D-glucopyranoside or 2'-thioethyl-α-D-glucopyranoside and said second ligand comprises 1-amino-17-mercapto-3,6,9,12,15,-pentaoxa-heptadecanol; or
  (d) said first ligand comprises 2'-thioethyl-2-acetamido-2-deoxy-β-D-glucopyranoside and said second ligand comprises 1-amino-17-mercapto-3,6,9,12,15,-pentaoxa-heptadecanol,
and wherein said first and second ligands are covalently
linked to the core via their respective sulphur atoms.

The nanoparticle in accordance with this aspect of the
invention may comprise a divalent component, such as a
metal or metal complex. One particularly useful component is
zinc. The divalent component may in some cases be present in
the corona of the nanoparticle. It is specifically contemplated
herein that the divalent component may be included in the
nanoparticle, including in the corona of the nanoparticle as a
result of inclusion of a divalent component in the process of
synthesis of the nanoparticle. Additionally or alternatively,
the divalent component may be added after synthesis of the
nanoparticle. In some cases in accordance with the present
invention, zinc may be used as the divalent component, where
the zinc may be selected from: $Zn^{2+}$ and ZnO. For example,
the zinc may be in the form of $ZnCl_2$. Other divalent materials, salts and oxides thereof, may be used as disclosed herein.
The component is desirably present in an amount sufficient to
produce a stabilizing effect and/or in an amount sufficient to
enhance the binding of the peptide to the corona to t level
great than the level of binding of the peptide to the corona in
the absence of the component having a divalent state. In some
cases, the component having a divalent state is desirably
present in an amount of about 0.5 to 2.0 equivalents to the core metal (e.g. gold), or optionally about 0.75 to 1.5 equivalents to the core metal (e.g. gold). In the context of the present invention, "equivalents" may be mole equivalents, for example 1.0 equivalent of zinc may be taken to mean the same number of zinc atoms or $Zn^{2+}$ cations as the number of gold atoms in the core of the nanoparticle.

In a further aspect the present invention provides a pharmaceutical composition comprising a plurality of nanoparticles of the invention and one or more pharmaceutically acceptable carriers or excipients. In some cases, the pharmaceutical composition may be formulated for administration to a mammalian subject by intraveneous (i.v.), intramuscular (i.m.), intradermal (i.d.) or subcutaneous (s.c) route.

In a further aspect the present invention provides a method of stabilising at least one peptide, comprising contacting the at least one peptide with a nanoparticle of the invention as defined herein under conditions which allow the at least one peptide to bind to the corona of the nanoparticle.

In a further aspect the present invention provides a method of lowering blood glucose in a mammalian subject in need thereof, comprising administering a therapeutically effective amount of a nanoparticle of the invention, for example a nanoparticle having insulin and/or GLP-1 bound to the corona.

In a further aspect the present invention provides a method of treating diabetes in a mammalian subject in need thereof, comprising administering a therapeutically effective amount of a nanoparticle of the invention, for example a nanoparticle having insulin and/or GLP-1 bound to the corona. The nanoparticle of the invention or a pharmaceutical composition comprising the nanoparticle may be administered to a subject by any suitable route of administration. In particular cases, the nanoparticle of the invention or pharmaceutical composition comprising said nanoparticle may be administered intraveneously (i.v.), intramuscularly (i.m.), intradermally (i.d.) or subcutaneously (s.c.).

In a further aspect the present invention provides a nanoparticle of the invention for use in a method of medical treatment. The nanoparticle may be formulated for pharmaceutical use, for example by combining one or, typically, a plurality of nanoparticles of the invention with one or more pharmaceutically acceptable excipients or carriers. The nanoparticle of the invention or pharmaceutical composition comprising said nanoparticle may be formulated for administration by any suitable route for delivery to a subject. In particular, the nanoparticle of the invention or pharmaceutical composition comprising said nanoparticle may be formulated for administration intraveneously (i.v.), intramuscularly (i.m.), intradermally (i.d.) or subcutaneously (s.c.).

In a further aspect the present invention provides a nanoparticle of the invention (for example a nanoparticle having insulin and/or GLP-1 bound to the corona) for use in a method of lowering blood glucose in a mammalian subject in need thereof and/or treating diabetes in a mammalian subject in need thereof.

In a further aspect the present invention provides use of a nanoparticle of the invention (for example a nanoparticle having insulin and/or GLP-1 bound to the corona) in the preparation of a medicament for use in a method of lowering blood glucose in a mammalian subject in need thereof and/or treating diabetes.

In a further aspect the present invention provides an article of manufacture comprising:
  at least one nanoparticle of the invention;
  a container for housing the at least one nanoparticle; and
  an insert and/or a label.

In a further aspect, the present invention provides a method for forming mesoscopic polypeptide or protein clusters, said clusters having embedded therein one or more nanoparticles of the invention, said method comprising contacting said polypeptide or protein with said one or more nanoparticles at an ambient temperature. In some cases the ambient temperature may be between 15° C. and 30° C., such as between 20° C. and 25° C.

In a further aspect, the present invention provides a method for dissociating one or more clusters, said one or more clusters comprising a cluster of mesoscopic peptide or protein having embedded therein one or more nanoparticles of the invention, said method comprising subjecting said clusters to a temperature from 35° C. to the melting temperature (Tm) of the peptide or protein thereby causing said one or more clusters to dissociate into individual nanoparticle-peptide flocculants.

In a further aspect, the present invention provides a method for releasing monomeric peptides from one or more nanoparticle-peptide flocculants in a solution, said method comprising increasing the ionic strength of the solvent, wherein said nanoparticle-peptide flocculants comprise one or more nanoparticles of the invention. In some cases, the method comprises dissolution of said one or more nanoparticle-peptide flocculants in a biological fluid, such as plasma, interstitial fluid or saliva.

The present invention includes the combination of the aspects and preferred features described except where such a combination is clearly impermissible or is stated to be expressly avoided. These and further aspects and embodiments of the invention are described in further detail below and with reference to the accompanying examples and figures.

Figure 12:
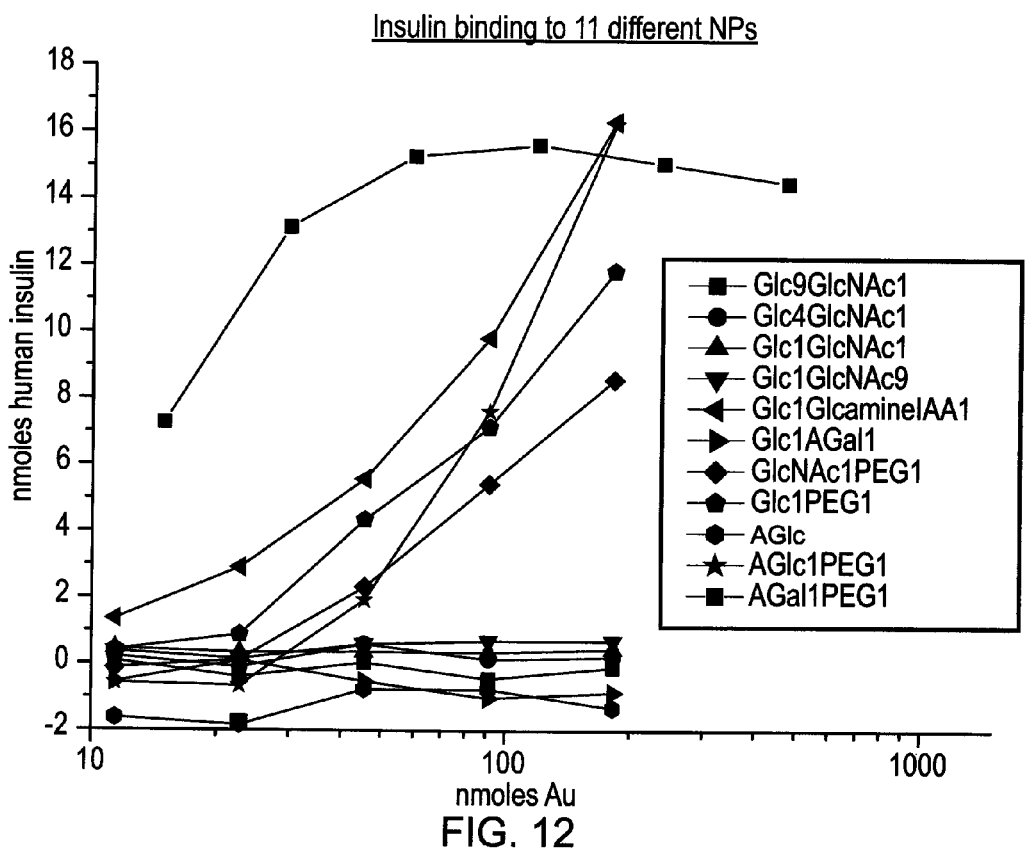
Figure 13:
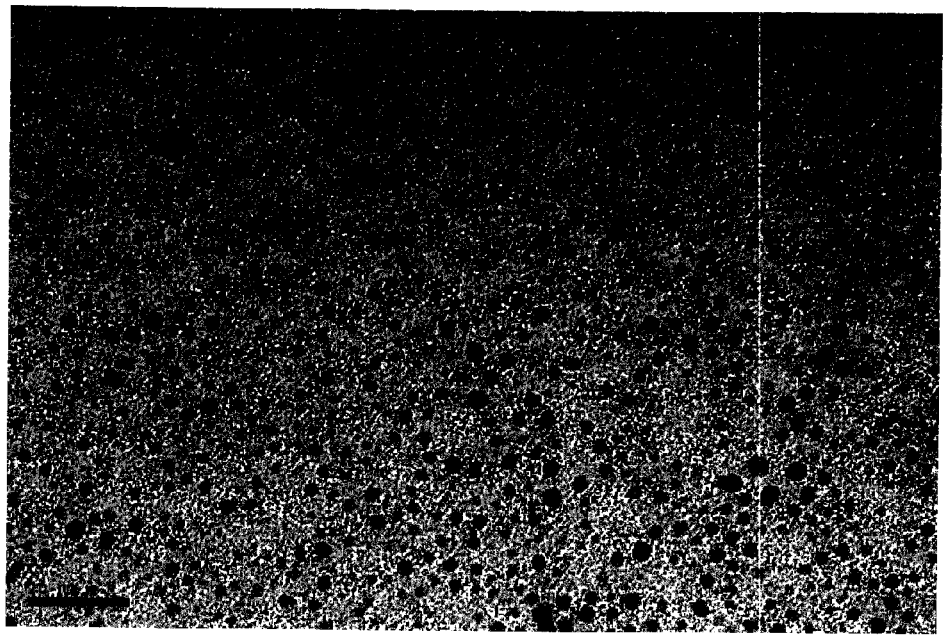
Figure 16:
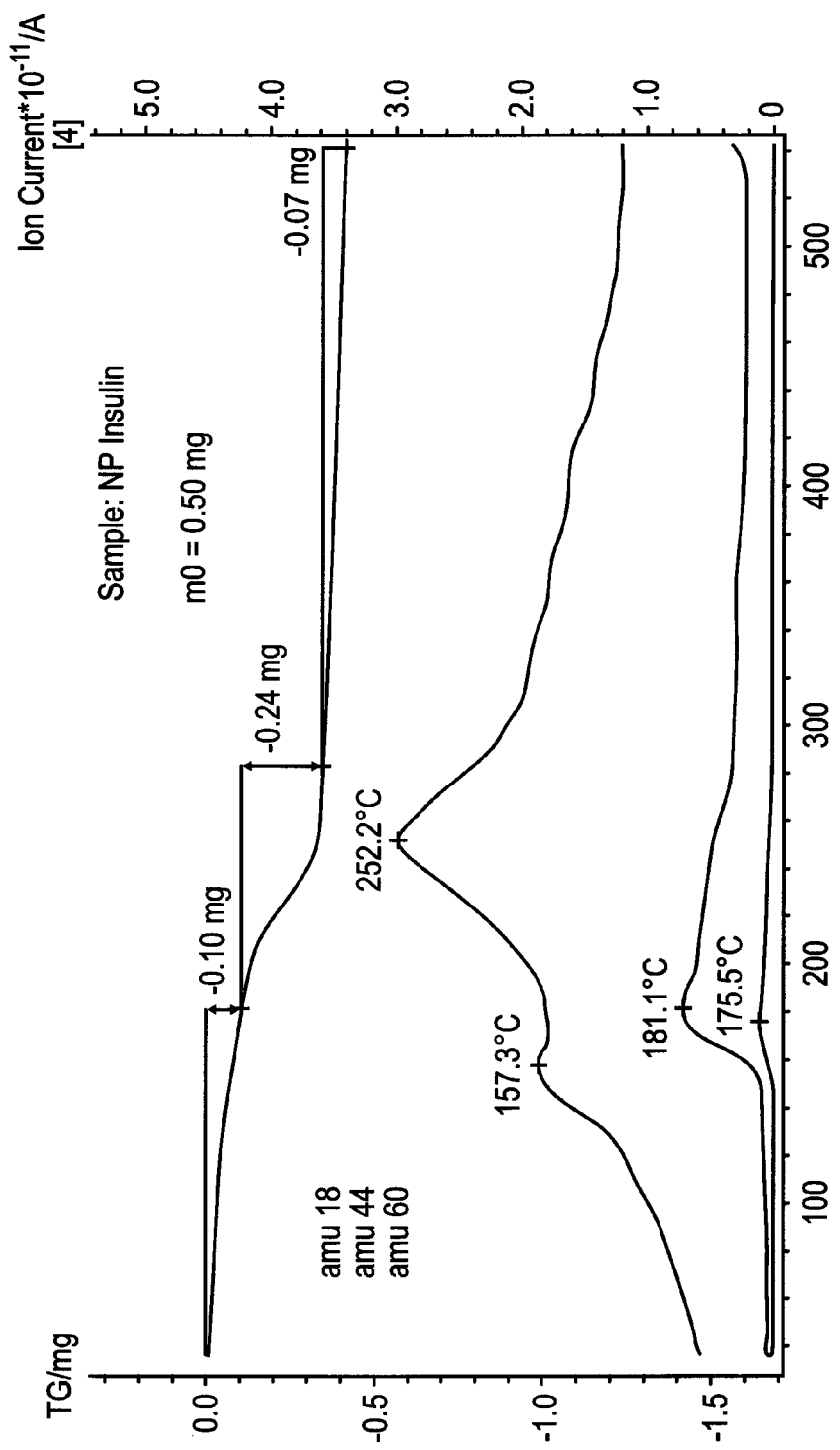
Figure 17:
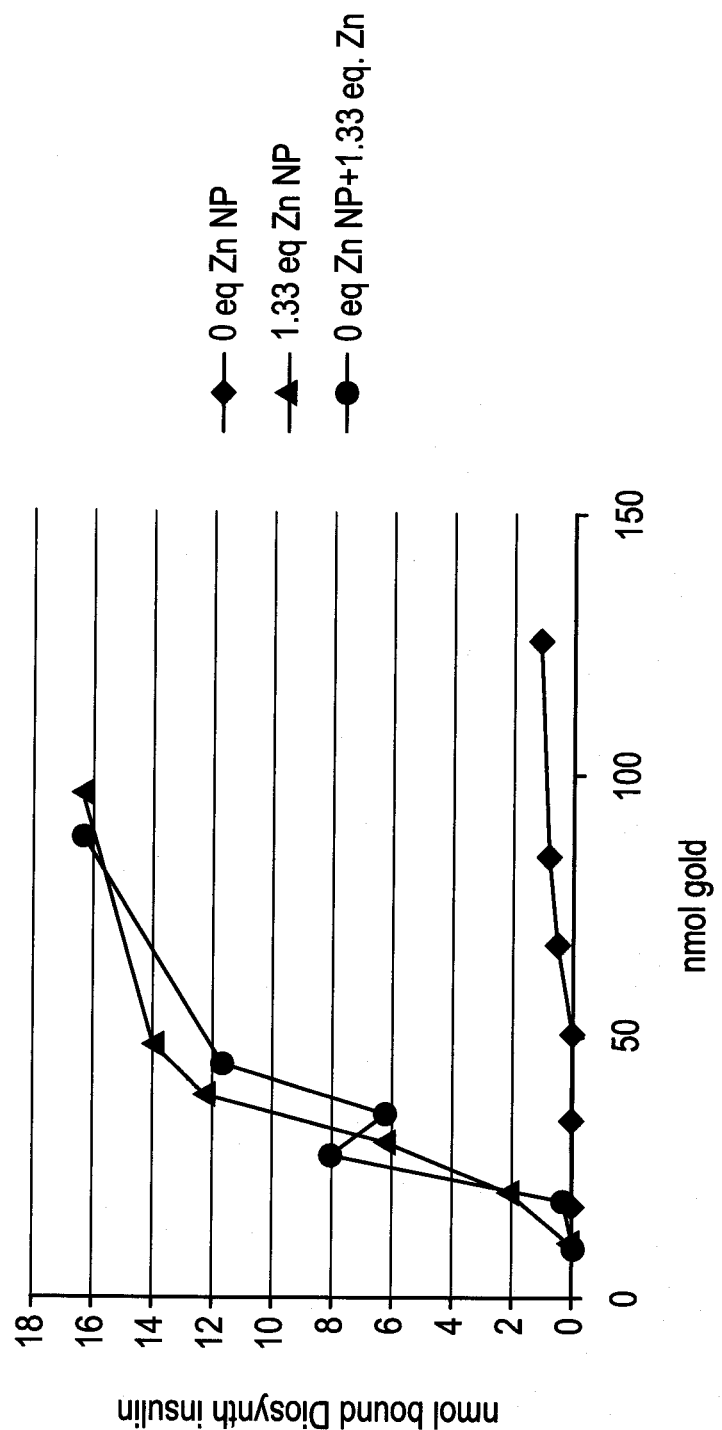
Figure 18:
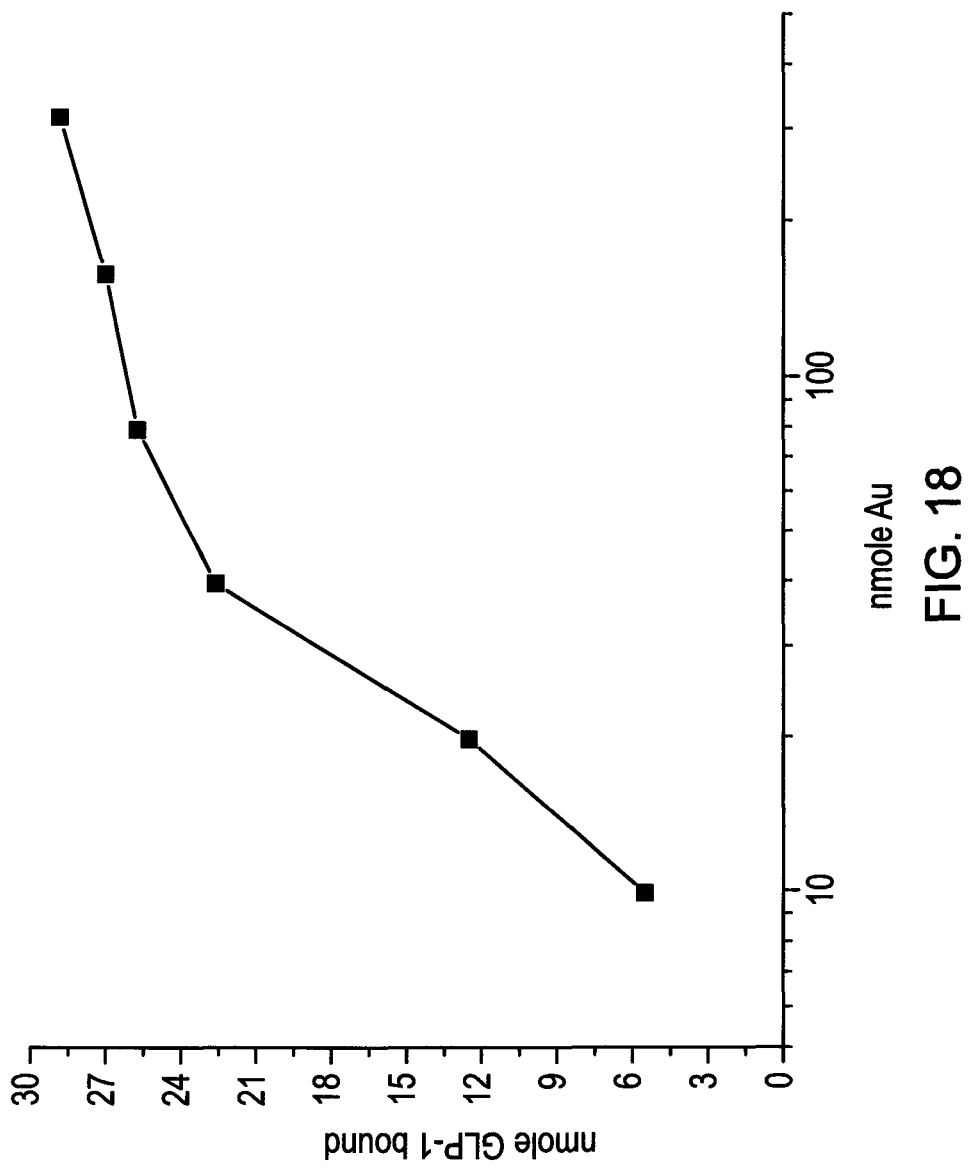
Figure 19:
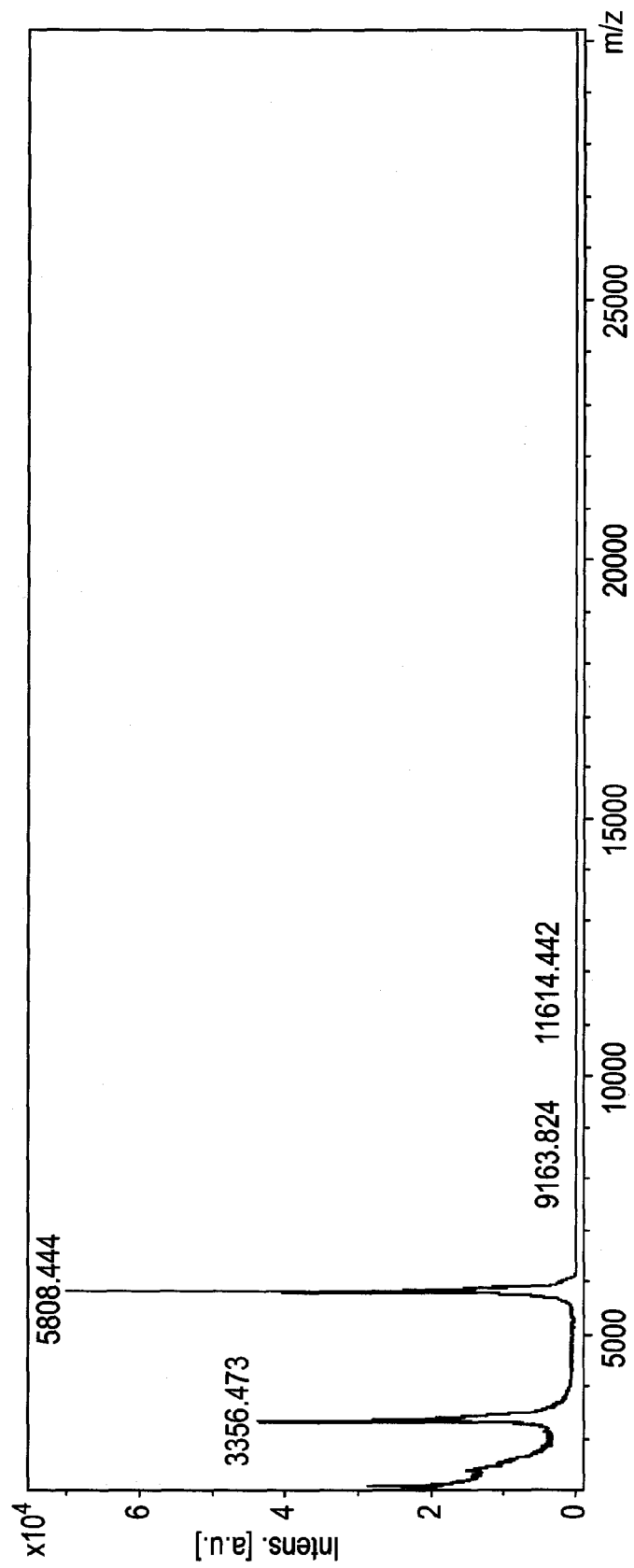
Figure 20:
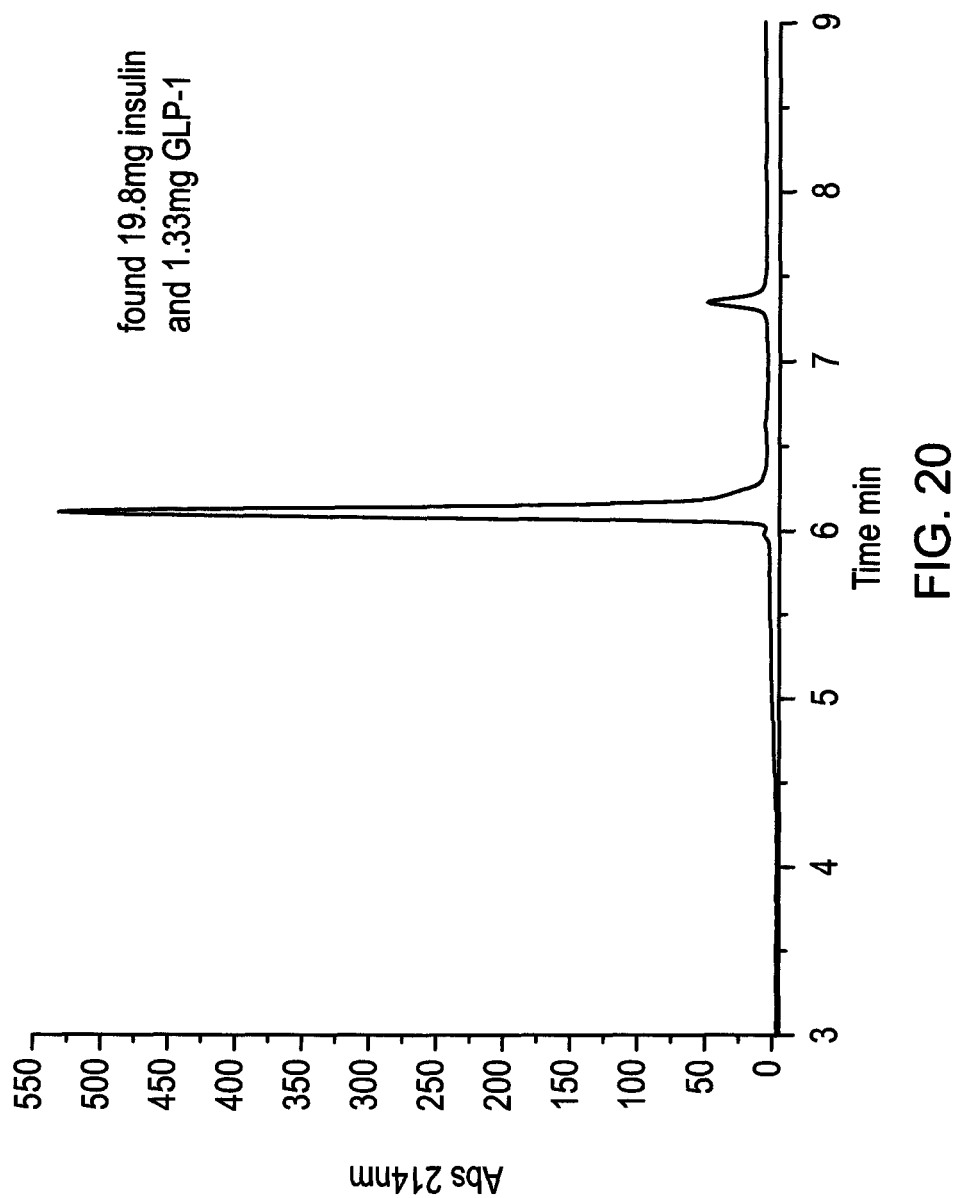

EG6NH2 "NP-alpha-Gal(1)EG6NH2(1)". In certain examples, the NP-alpha-Gal(1)EG6NH2(1) nanoparticles are referred to herein as batch NP10;

FIG. 12 shows insulin binding curves of human insulin bound (in nmoles) per amount of gold (in nmoles) for 11 different nanoparticle coronal compositions;

FIG. 13 shows a transmission electron microscopy (TEM) image NP-alpha-Gal(1)EG6NH2(1) nanoparticles {batch #NP10};

FIG. 14 shows size distribution plots determined by dynamic light scattering (DLS) for MI-NP-10 amine-gal (i.e. NP-alpha-Gal(1)EG6NH2(1) nanoparticles) by, A) number and B) volume;

FIG. 15 shows size distribution plots determined by dynamic light scattering (DLS) for insulin bound-MI-NP-10 amine-gal (i.e. NP-alpha-Gal(1)EG6NH2(1) nanoparticles) by A) number and B) volume;

FIG. 16 shows experimental thermogravimetric analysis (TGA) data for α-galactose-EG-amine-Au nanoparticles with temperature peaks indicated {batch #NP10};

FIG. 17 shows a graph of insulin bound to gold nanoparticles, wherein diamonds indicate nanoparticles in the absence of zinc, triangles indicate nanoparticles synthesized in the presence of 1.33 equivalents of zinc, and circles indicate nanoparticles synthesized in the absence of zinc to which 1.33 equivalents of zinc have been added post-synthesis;

FIG. 18 shows binding of GLP-1 to gold nanoparticles at varying amounts of gold nanoparticles;

FIG. 19 shows a MALDI trace showing GLP-1 and insulin from a nanoparticle preparation comprising both GLP-1 and insulin;

FIG. 20 shows an HPLC trace showing GLP-1 and insulin from a nanoparticle preparation comprising both GLP-1 and insulin.

DETAILED DESCRIPTION OF THE INVENTION

In describing the present invention, the following terms will be employed, and are intended to be defined as indicated below.

As used herein, "nanoparticle" refers to a particle having a nanomeric scale, and is not intended to convey any specific shape limitation. In particular, "nanoparticle" encompasses nanospheres, nanotubes, nanoboxes, nanoclusters, nanorods and the like. In certain embodiments the nanoparticles and/or nanoparticle cores contemplated herein have a generally polyhedral or spherical geometry.

Nanoparticles comprising a plurality of carbohydrate-containing ligands have been described in, for example, WO 2002/032404, WO 2004/108165, WO 2005/116226, WO 2006/037979, WO 2007/015105, WO 2007/122388, WO 2005/091704 (the entire contents of each of which is expressly incorporated herein by reference) and such nanoparticles may find use in accordance with the present invention. Moreover, gold-coated nanoparticles comprising a magnetic core of iron oxide ferrites (having the formula $XFe_2O_4$, where X=Fe, Mn or Co) functionalised with organic compounds (e.g. via a thiol-gold bond) are described in unpublished European patent application No. EP09382185.8 filed 25 Sep. 2009 (the entire contents of which is expressly incorporated herein by reference) and are specifically contemplated for use as nanoparticles/nanoparticle cores in accordance with the present invention.

As used herein, "corona" refers to a layer or coating, which may partially or completely cover the exposed surface of the nanoparticle core. The corona includes a plurality of ligands which include at least one carbohydrate moiety. Thus, the corona may be considered to be an organic layer that surrounds or partially surrounds the metallic core. In certain embodiments the corona provides and/or participates in passivating the core of the nanoparticle. Thus, in certain cases the corona may include a sufficiently complete coating layer substantially to stabilise the metal-containing core. However, it is specifically contemplated herein that certain nanoparticles having cores, e.g., that include a metal oxide-containing inner core coated with a noble metal may include a corona that only partially coats the core surface.

As used herein, "peptide" is intended to encompass any sequence of amino acids and specifically includes peptides, polypeptides proteins (including proteins having secondary, tertiary and/or quaternary structure) and fragments thereof. The expression "peptide bound to" is specifically intended to encompass a part (but may include the whole) of the amino acid sequence of the peptide forming a bonding interaction with one or more parts (such as a chemical group or moiety) of one or more of the plurality of ligands of the nanoparticle. In certain embodiments the peptide may have a molecular weight of <500 kDa, <100 kDa, <50 kDa, such as up to 20 kDa.

Accordingly, in one aspect the present invention provides a nanoparticle comprising:
(i) a core which includes a metal;
(ii) a corona which includes a plurality of ligands covalently linked to the core, wherein at least one of said ligands includes a carbohydrate moiety; and
(iii) at least one peptide bound to the corona.

The term "bound" is intended to include a physical and/or a chemical association between two components. This term includes any form of chemical linkage, e.g., covalent, ionic, hydrogen bonding or intermolecular forces, such as van der Waals forces or electrostatic forces. The term includes physical coupling or linking. This physical and or chemical association may be intended to be reversible, i.e., the component may be separated or disassociated, one from the other, e.g., to release the active component from the carrier component.

The peptide may be reversibly bound to the corona. In particular it is specifically contemplated that the peptide may be bound to a part of the nanoparticle non-covalently. Without wishing to be bound by any theory, it is presently believed that a peptide may participate in one or more reversible binding interactions with one or more ligands that provide the corona of the nanoparticle. In particular, a portion of the sequence of amino acids may participate in hydrogen bonding, Van der Waals forces and/or electrostatic interactions with one or more ligands (e.g. interacting with one or more functional groups of an exposed ligand). The peptide binding may involve adsorption, absorption or other direct or indirect interaction with one or more ligands of the nanoparticle.

As described herein with reference to certain embodiments of the present invention, the peptide may be bound such that at least a fraction or portion of the bound peptide is released from the nanoparticle upon contacting the nanoparticle with a physiological solution. As described herein the peptide may be bound to the nanoparticle in a manner such that the peptide is stabilised (e.g. thermostabilised) while bound, but is releasable and available in a form that is biologically active (for example, releasable such that the peptide is detectable by ELISA and/or capable of exerting at least one biological action in an in vitro or in vivo system that is characteristic of the free peptide). In particular, when the peptide includes (human) insulin, the peptide may be bound to the nanoparticle such that a suspension of the insulin-bound nanoparticles gives a positive result in an ELISA for (human) insulin and/or exerts an effect on blood glucose levels in a mammalian subject following administration thereto.

A variety of release kinetics are contemplated for dissociation of bound peptide molecule(s) from the nanoparticle, including bi- or multi-phase release (such as an initial fast release followed by a slower subsequent release phase). For example, the release may include dissociation of bound peptide molecules from the nanoparticle rapidly within seconds or minutes followed by further sustained release over a period of at least 2, 4, 6, 8 or more hours. Such release kinetics may be advantageous in certain circumstances, e.g. where sustained action is desired, in comparison with, e.g., an injection of free peptide.

The peptide (including without limitation polypeptide, protein, or fragment thereof) may be selected from the group consisting of: insulin, GLP-1, IGF1, IGF2, relaxin, INSL5, INSL6, INSL7, pancreatic polypeptide(PP), peptide tyrosine tyrosine (PTT), neuropeptide Y, oxytocin, vasopressin, GnRH, TRH, CRH, GHRH/somatostatin, FSH, LH, TSH, CGA, prolactin, CIIP, ACTH, MSH, endorphins, lipotropin, GH, calcitonin, PTH, inhibin, relaxin, hCG, HPL, glucagons, somatostatin, melatonin, thymosin, thmulin, gastrin, ghrelin, thymopoietin, CCK, GIP secretin, motin VIP, enteroglucagon, leptin, adiponectin, resistin, osteocalcin, renin, EPO, calicitrol, ANP, BNP, chemokines, cytokines, adipokines and biologically active analogs thereof. In certain embodiments the peptide is capable of stimulating a reduction in blood glucose levels in a mammalian subject. Thus, in some cases in accordance with the present invention the peptide may include monomeric and/or dimeric human insulin.

In certain cases in accordance with the present invention there may be at least 1, at least 2, at least 3, at least 4, at least 5, at least 10 or more peptide molecules bound per core on average. There may be a single type of peptide or two or more different peptides. Where a combination of two different peptides are bound to a nanoparticle, the different peptides may in some cases be present in a ratio of 1:10 to 10:1, such as 1:2 to 2:1. Thus, complementary combinations of peptides that are advantageously co-administered are specifically contemplated.

As used herein the term "carbohydrate" is intended to include compounds of the general formula $C_n(H_2O)_m$ where n=m and n is greater than 3. Also, included within the definition of carbohydrate are carbohydrate analogues/mimetics that are not included in the general formula $C_n(H_2O)_m$. The carbohydrate analogues/mimetics include but are not limited to pseudo-sugars (carba-sugars), amino-sugars, imino-sugars and inositols. Amino-sugars include polyhydroxylated piperidines, pyrrolidines, pyrrolizidines and indolizidines.

As described herein the nanoparticle in accordance with the present invention includes a plurality of ligands covalently linked to a metal-containing core. The ligands may be the same or different. In particular embodiments, the plurality of ligands may include a first class of ligands including at least one carbohydrate moiety and a second class of non-carbohydrate ligands. As used herein the at least one ligand including carbohydrate moiety will generally include one or more sugar groups, such as a monosaccharide, a disaccharide and/or a polysaccharide and/or one or more pseudo-sugar groups (such as pseudo sugar selected from: a carba-sugar, an amino-sugar, an imino-sugar, an inositol, a polyhydroxylated piperidine, a pyrrolidine, a pyrrolizidine and an indolizidine). The ligands are covalently linked to the core of the nanoparticle. Therefore, the term "carbohydrate moiety" is to be understood to include chemical derivatives of carbohydrates such as glycosides wherein the ligand includes a sugar group or pseudo-sugar group (such as pseudo sugar selected from: a carba-sugar, an amino-sugar, an imino-sugar, an inositol, a polyhydroxylated piperidine, a pyrrolidine, a pyrrolizidine and an indolizidine) attached to a non-sugar atom or molecule. In particular cases, the ligand including a carbohydrate moiety in accordance with the present invention may include a glycoside of galactose, glucose, glucosamine, N-acetylglucosamine, mannose, fucose and/or lactose, e.g. the carbohydrate moiety may include a galactopyranoside and/or a glucopyranoside. The carbohydrate-containing ligand may be covalently linked to the core via a linker selected from sulphur-containing linkers, amino-containing linkers and phosphate-containing linkers. Combinations of linkers off of the core may also be used. The linker may in some cases include an alkyl chain of at least two carbons.

The ligand linked to the core includes one or more carbohydrate (saccharide) groups, e.g. including a polysaccharide, an oligosaccharide or a single saccharide group. The ligand may also be a glycanoconjugate such as a glycolipid or a glycoprotein. In addition to the carbohydrate group, the ligand may additionally include one or more of a peptide group, a protein domain, a nucleic acid molecule (e.g. a DNA/RNA segment) and/or a fluorescent probe.

In certain cases the particles may have more than one species of ligand immobilised thereon, e.g. 2, 3, 4, 5, 10, 20 or 100 different ligands. Alternatively or additionally a plurality of different types of particles can be employed together.

In certain cases, the mean number of ligands linked to an individual metallic core of the particle is at least 5, at least 10 or at least 20 ligands. The number may be in the range 10 to 10,000 such as 10 to 1,000, more particularly 20 to 500 or 44 to 106 ligands per core.

Preferably, substantially all of the ligands are attached covalently to the core of the particles. Protocols for carrying this out are known in the art (see, e.g. WO 2002/032404, WO 2004/108165, WO 2005/116226, WO 2006/037979, WO 2007/015105, WO 2007/122388, WO 2005/091704). This may be carried out by reacting ligands with reductive end groups with a noble metal such as gold under reducing conditions. An exemplary method of producing the particles employs thiol derivatised carbohydrate moieties to couple the ligands to particles. Thus, the ligand is derivatised as a protected disulphide. Conveniently, the disulphide protected ligand in methanol can be added to an aqueous solution of tetrachloroauric acid. A preferred reducing agent is sodium borohydride. In certain embodiments, the nanoparticles are soluble in organic solvents and in water and physiological solutions. The present inventors have found that the nanoparticles as described herein are suitable for therapeutic applications, and may be non-toxic, soluble and/or excreted in the urine.

In certain cases in accordance with the present invention, the at least one ligand comprising a carbohydrate moiety is selected from the group of: 2'-thioethyl-α-D-galactopyranoside, 2'-thioethyl-β-D-glucopyranoside, 2'-thioethyl-2-acetamido-2-deoxy-β-D-glucopyranoside, 5'-thiopentanyl-2- deoxy-2-imidazolacetamido-α,β-D-glucopyranoside and 2'-thioethyl-α-D-glucopyranoside, and wherein said at least one ligand comprising a carbohydrate moiety is covalently linked to the core via the thiol sulphur.

Additionally or alternatively, the plurality of ligands may include an amine group. Thus, a ligand comprising a carbohydrate group may include an amine group (e.g. as part of the carbohydrate, such as a glucosamine, and/or as a constituent group of a non-carbohydrate part of the ligand. Moreover, where the plurality of ligands includes at least one non-carbohydrate ligand, the non-carbohydrate group may include an amine group. The at least one non-carbohydrate ligand may include 1-amino-17-mercapto-3,6,9,12,15,-pentaoxa-heptadecanol covalently linked to the core via the thiol sulphur.

In accordance with certain embodiments of the present invention, the plurality of ligands may include said at least one ligand including a carbohydrate moiety and said at least one non-carbohydrate ligand wherein the said ligands are different and are present on the nanoparticle in a ratio of 1:40 to 40:1, such as a ratio of 1:10 to 10:1, more particularly a ratio of 1:2 to 2:1.

The nanoparticle "core" includes a metal. Suitable cores are described in, e.g., WO 2002/032404, WO 2004/108165, WO 2005/116226, WO 2006/037979, WO 2007/015105, WO 2007/122388, WO 2005/091704 (the entire contents of each of which is expressly incorporated herein by reference) and such nanoparticle cores may find use in accordance with the present invention. Moreover, gold-coated nanoparticles including a magnetic core of iron oxide ferrites (having the formula $XFe_2O_4$, where X=Fe, Mn or Co) are described in unpublished European patent application No. EP09382185.8 filed 25 Sep. 2009 (the entire contents of which is expressly incorporated herein by reference) and may find use in accordance with the present invention.

In some cases in accordance with the present invention the nanoparticle core includes a metal selected from the group of: Au, Ag, Cu, Pt, Pd, Fe, Co, Gd, Zn or any combination thereof. The core may include a passive metal selected from the group of: Au, Ag, Pt, Pd and Cu, or any combination thereof. In certain embodiments a specific combination of metals may be employed, such as a combination of metals selected from the group of: Au/Fe, Au/Ag, Au/Cu, Au/Ag/Cu, Au/Pt, Au/Pd, Au/Ag/Cu/Pd, Au/Gd, Au/Fe/Cu, Au/Fe/Gd, Au/Fe/Cu/Gd.

In some cases in accordance with the present invention the nanoparticle core may be magnetic. The core may include an NMR active atom, such as a metal selected from the group of: $Mn^{2+}$, $Gd^{3+}$, $Eu^{2+}$, $Cu^{2+}$, $V^{2+}$, $Co^{2+}$, $Ni^{2+}$, $Fe^{3+}$ and lanthanides$^{3+}$.

In some cases in accordance with the present invention the nanoparticle core may include a semiconductor, such as that selected from the group of: cadmium selenide, cadmium sulphide, cadmium tellurium and zinc sulphide.

In some cases in accordance with the present invention the nanoparticle core may include a metal oxide coated with a metal selected from the group of: Au, Ag, Cu, Pt, Pd and Zn, or any combination thereof. The metal oxide may advantageously be of the formula $XFe_2O_4$, where X is a metal selected from the group of: Fe, Mn and Co.

In some cases in accordance with the present invention the nanoparticle core may have an average diameter in the range of about 0.5 nm to about 50 nm, such as about 1 nm to about 10 nm, more specifically about 1.5 nm to about 2 nm.

The following is presented by way of example and is not to be construed as a limitation to the scope of the claims.

EXAMPLES

Example 1

Preparation of Ligands

Preparation of 2-thio-ethyl-α-D-galactoside (α-galactose C2SH)

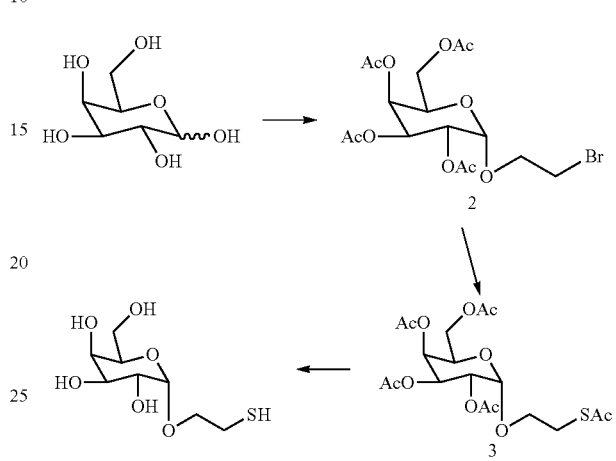

To a suspension of galactose (3 g, 16.65 mmol) in 2-bromoethanol (30 ml), acid resin Amberlite 120H is added to reach pH 2. The reaction is stirred for 16 hours at 50-60° C. The reaction mixture is filtered and washed with MeOH. Triethylamine is added to reach pH 8. The crude of the reaction is concentrated and co evaporated 3 times with toluene. The reaction mixture is dissolved pyridine (75 mL) and Ac2O (35 mL) and a catalytic amount of DMAP are added at 0° C. and stirred for 3 h at rt. The mixture is diluted with AcOEt and washed with 1. $H_2O$; 2. HCl (10%) 3. $NaHCO_3$ dis 4. $H_2O$. The organic layer is collected and dried over anhydrous $Na_2SO_4$. TLC (Hexane:AcOEt 3:1, 2 elutions) shows a major product (desired) and a lower Rf minority. The product is purified by flash chromatography using the mixture hexane: ethyl acetate 6:1 as eluent and the 2-bromoethyl-alpha-galactoside (2) is obtained.

The product of the previous reaction, 2 is dissolved in 27 ml of 2-butanone. To this solution, a catalytic amount of tetrabutylammonium iodide and 4 equivalents of potassium thioacetate are added. The resulting suspension is stirred for 2 hours at room temperature. Throughout this period the reaction is tested by TLC (hexane-AcOEt 2:1, 2 elutions) for the disappearance of the starting material. The mixture is diluted with 20 ml of AcOEt and washed with a saturated NaCl solution. The organic phase is dried, filtered and evaporated under vacuum. The product is purified in hexane/AcOEt 2:1→1:1 to obtain the acetylthio-alpha-galactoside 3.

The new product of the reaction, 3 is dissolved in a mixture dichloromethane-methanol 2:1. To this mixture a solution of 1N sodium methoxide (1 equivalent) is added and stirred for 1 hour at room temperature. Amberlite IR-120H resin is added to achieve pH 5-6. The resulting mixture is then filtered and concentrated to dryness to obtain the final product (α-galactose C2SH).

Preparation of Amino-Thiol Linker

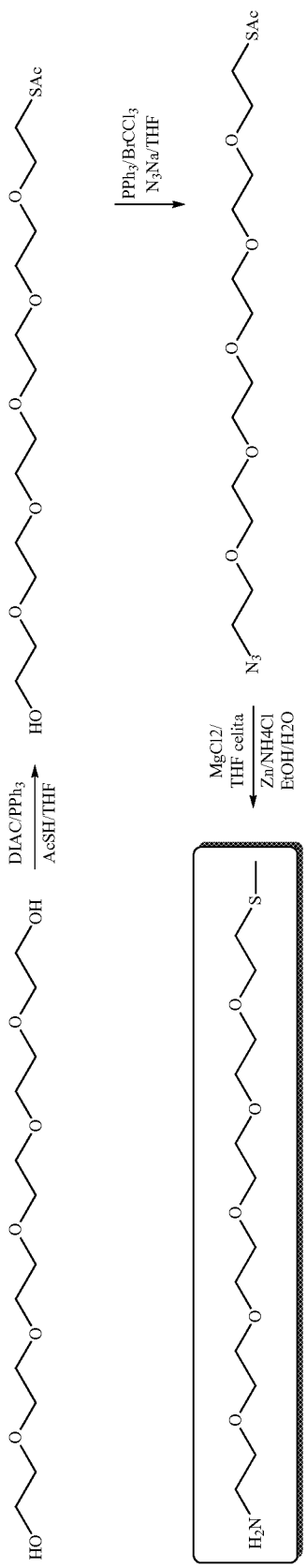

To a solution of PPh₃ (3 g, 11.4 mmol) in 20 ml dry THF, DIAC (2.3 g, 11.4 mmol) is added. The mixture is allowed to stir at 0° C. 15 min until the appearance of a white product. To this mixture a solution of hexaethyleneglycol (1.45 mL, 5.7 mmol) and HSAc (610 μl, 8.55 mmol) in dry THF (20 mL) is added dropwise (addition funnel). After 15 min the products begin to appear on TLC at Rf 0.2. The solution is concentrated in an evaporator. The crude of the reaction is dissolved in 50 ml of dichloromethane and washed with a solution of $K_2CO_3$ 10%. The organic phase is dried over anhydrous $Na_2SO_4$, filtered and concentrated under vacuum. Flash chromatography of the crude using AcOEt:Hexane 1:1, AcOEt and finally DCM:MeOH 4:1 as eluyent gave the acetyl-thio-hexaethyleneglycol derivative.

The reaction product is dissolved in 5 ml of DMF and PPh₃ (2.25 g, 8.55 mmol), NaN₃ (0.741 g, 11.4 mmol) and BrCl₃C (0,845 ml, 8.55 mmol) are added and the solution subsequently stirred for 40 min at room temperature. The resulting product has a higher Rf than the starting product when performing TLC (DCM:MeOH 25:1). The reaction mixture is diluted with 100 ml of diethylether and washed three times with H₂O. The organic phase is dried over anhydrous $Na_2SO_4$, filtered and evaporated under vacuum. The product is purified by flash chromatography using the mixture of eluents DMC/MeOH 200:1 and DCM/NeOH 40:1 to obtain the azido-acetylthio-hexaethyleneglycol derivative.

To remove the triphenyl phosphine oxide, the reaction product is dissolved in 10 ml of THF and 0.5 g of MgCl₂ is added to this solution. The reaction is stirred for 2 h at 80° C. until a white precipitate appears and then is filtered through celite.

The product is dissolved in a mixture of ethanol:H₂O 3:1 and added Zn dust (0.45 g, 6.84 mmol) and NH₄Cl (0.6 g, 11.4 mmol). The reaction was stirred at reflux for 1 h until the presence of starting material is no longer detectable by TLC (DCM/MeOH 25:1). The reaction is filtered through celite and the solvent is evaporated. The crude de reaction is diluted with AcOEt and extract with 5 ml H₂O. The aqueous phase is evaporated to dryness to obtain the amino-thiol-hexaethylenglycol product.

Example 2

Preparation of Mixed Gold Nanoparticles

Beta-glucose C2 derivative 1, N-acetylglucosamine C2 derivative 2, alpha-galactose C2 derivative 3, alpha-glucose C2 derivative 4, glucosamine C5 derivative 5 and hexaethyleneglycol amine linker 6 were taken from Midatech Biogune stock. N-(3-Dimethylaminopropyl)-N'-ethylcarbodiimide hydrochloride (EDC.HCl), HAuCl₄, NaBH₄ were purchased from Sigma-Aldrich Chemical Company. Imidazole-4-acetic acid monohydrochloride was purchased from Alfa Aesar. Company High quality MeOH and Nanopure water (18.1 mΩ) were used for all experiments and solutions.

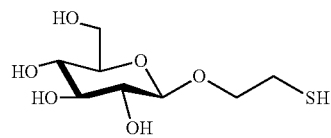

1

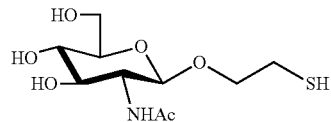

2'-thioethyl-β-D-glucopyranoside (beta)

GlcNHAcC2

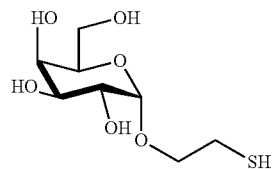

2'-thioethyl-2-acetamido-2-deoxy-β-D-glucopyranoside (beta)

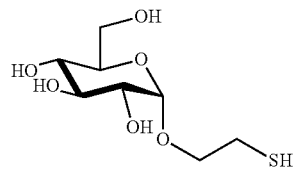

3

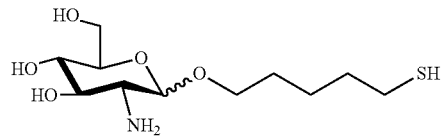

4

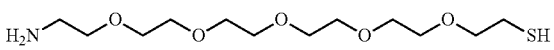

5

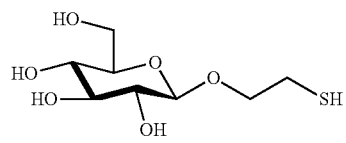

6

Nomenclature of the Ligands

GlcC2

GlcNH2-IAA-C5

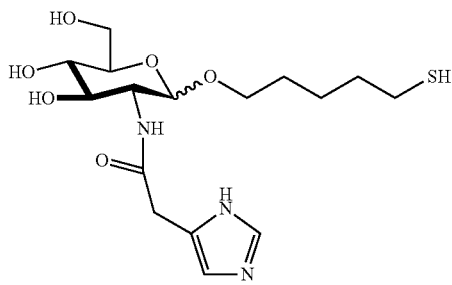

5'-thiopentanyl-2-deoxy-2-imidazolacetamido-α,β-D-glucopyranoside (alpha, beta mix of isomers)
α-GalC2 (Alpha)

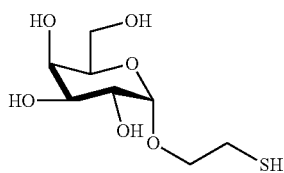

2'-thioethyl-α-D-galactopyranoside (alpha)
α-GlcC2 (Alpha)

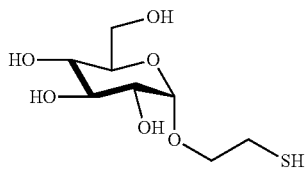

2'-thioethyl-α-D-glucopyranoside
EG6NH2

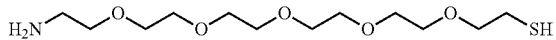

1-amino-17-mercapto-3,6,9,12,15,-pentaoxa-heptadecanol
or
1-amino-6-mercapto-hexaethylenglycol (vulgar name)

Preparation of Nanoparticles (NP) having a Plurality of Ligands

NP-GlcC2(9)GlcNAc(1)

To a solution of 1 (21.6 mg, 90 μmol) and 2 (2.8 mg, 10 μmol) in MeOH (8.3 mL) a 0.025M aqueous solution of HAuCl₄ (1.33 mL, 33 μmol) was added. The solution was shaken during 30 seconds and then an aqueous solution of NaBH₄ 1N (0.67 mL, 0.67 mmol) was added in several portions (134 μL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.). The process was repeated three times, washing with 2 mL of water. The residue was dissolved in 7 mL of water. An aliquot was freeze dried for quantitation. [NP]=0.8 mg/mL.

Figure 1:
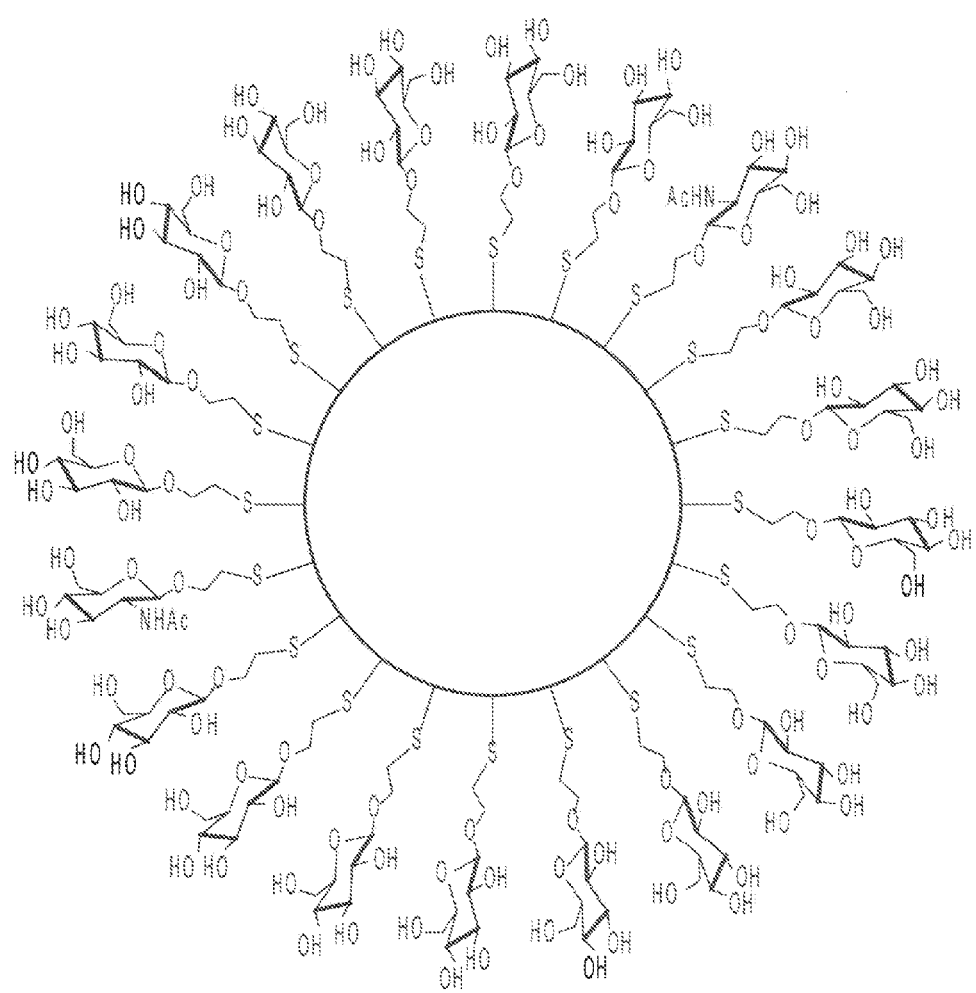
FIG. 1 shows a schematic representation of nanoparticles having a plurality of ligands in the ratio 9:1 of GlcC2:GlcNAc "NP-GlcC2(9)GlcNAc(1)"

Without wishing to be bound by any theory, a schematic representation of the resulting nanoparticles having a plurality of ligands in the ratio 9:1 of GlcC2:GlcNAc "NP-GlcC2 (9)GlaNAc(1)" is shown in FIG. 1.

NP-GlcC2(4)GlcNAc(1)

To a solution of 1 (19.2 mg, 80 μmol) and 2 (5.6 mg, 20 μmol) in MeOH (8.3 mL) a 0.025M aqueous solution of HAuCl₄ (1.33 mL, 33 μmol) was added. The solution was shaken during 30 seconds and then an aqueous solution of NaBH₄ 1N (0.67 mL, 0.67 mmol) was added in several portions (134 μL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.). The process was repeated three times, washing with 2 mL of water. The residue was dissolved in 7 mL of water. An aliquot was freeze dried for quantitation. [NP]=0.8 mg/mL.

Figure 2:
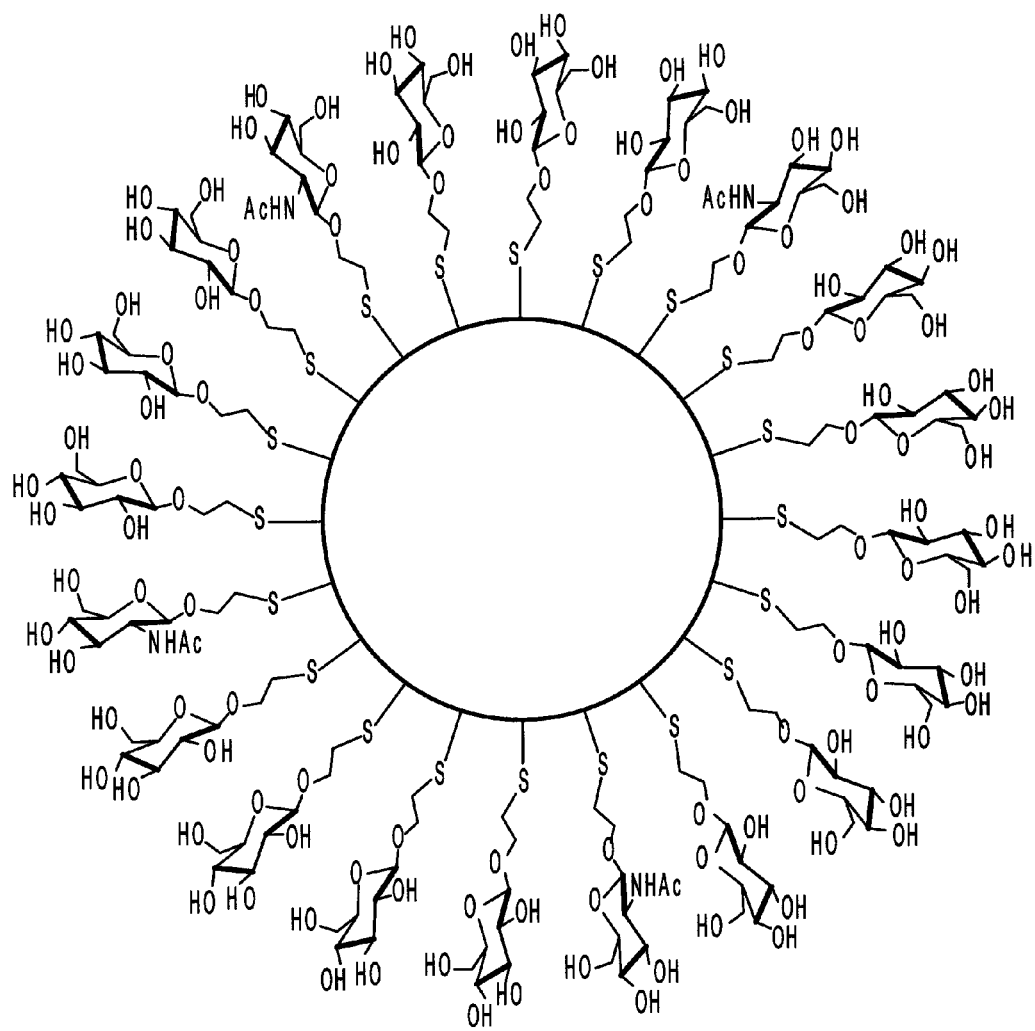
FIG. 2 shows a schematic representation of nanoparticles having a plurality of ligands in the ratio 4:1 of GlcC2:GlcNAc "NP-GlcC2(4)GlcNAc(1)"

Without wishing to be bound by any theory, a schematic representation of the resulting nanoparticles having a plurality of ligands in the ratio 4:1 of GlcC2:GlcNAc "NP-GlcC2 (4)GlcNAc(1)" is shown in FIG. 2.

NP-GlcC2(1)GlcNAc(1)

To a solution of 1 (12 mg, 50 μmol) and 2 (14 mg, 50 μmol) in MeOH (8.3 mL) a 0.025M aqueous solution of HAuCl₄ (1.33 mL, 33 μmol) was added. The solution was shaken during 30 seconds and then an aqueous solution of NaBH₄ 1N (0.67 mL, 0.67 mmol) was added in several portions (134 μL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.). The process was repeated three times, washing with 2 mL of water.

The residue was dissolved in 7 mL of water. An aliquot was freeze dried for quantitation. [NP]=0.9 mg/mL.

Figure 3:
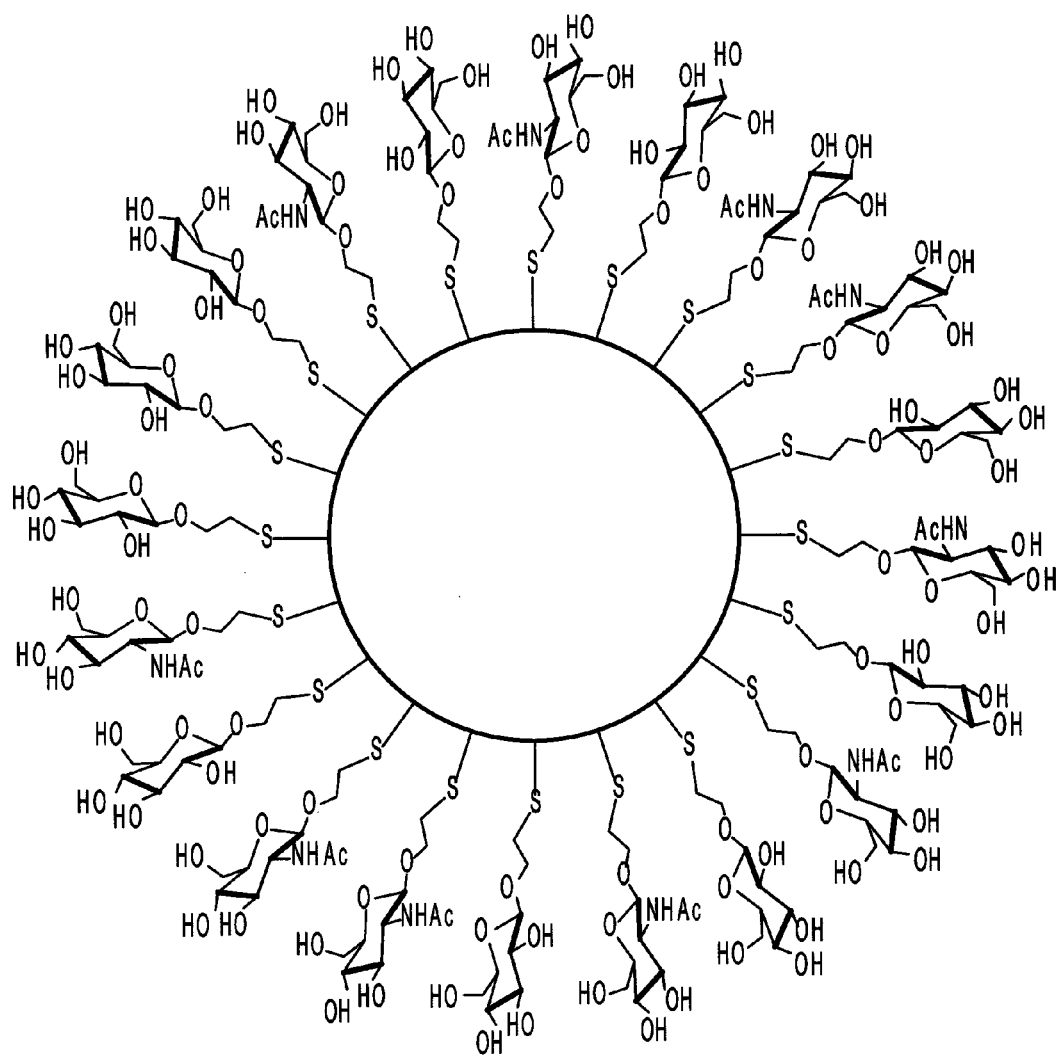
FIG. 3 shows a schematic representation of nanoparticles having a plurality of ligands in the ratio 1:1 of GlcC2:GlcNAc "NP-GlcC2(1)GlcNAc(1)"

Without wishing to be bound by any theory, a schematic representation of the resulting nanoparticles having a plurality of ligands in the ratio 1:1 of GlcC2:GlcNAc "NP-GlcC2 (1)GlcNAc(1)" is shown in FIG. 3.

NP-GlcC2(1)GlcNAc(9)

To a solution of 1 (2.4 mg, 10 μmol) and 2 (25.3 mg, 90 μmol) in MeOH (8.3 mL) a 0.025M aqueous solution of HAuCl₄ (1.33 mL, 33 μmol) was added. The solution was shaken during 30 seconds and then an aqueous solution of NaBH₄ 1N (0.67 mL, 0.67 mmol) was added in several portions (134 μL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.). The process was repeated three times, washing with 2 mL of water. The residue was dissolved in 7 mL of water. An aliquot was freeze dried for quantitation. [NP]=0.8 mg/mL.

Figure 4:
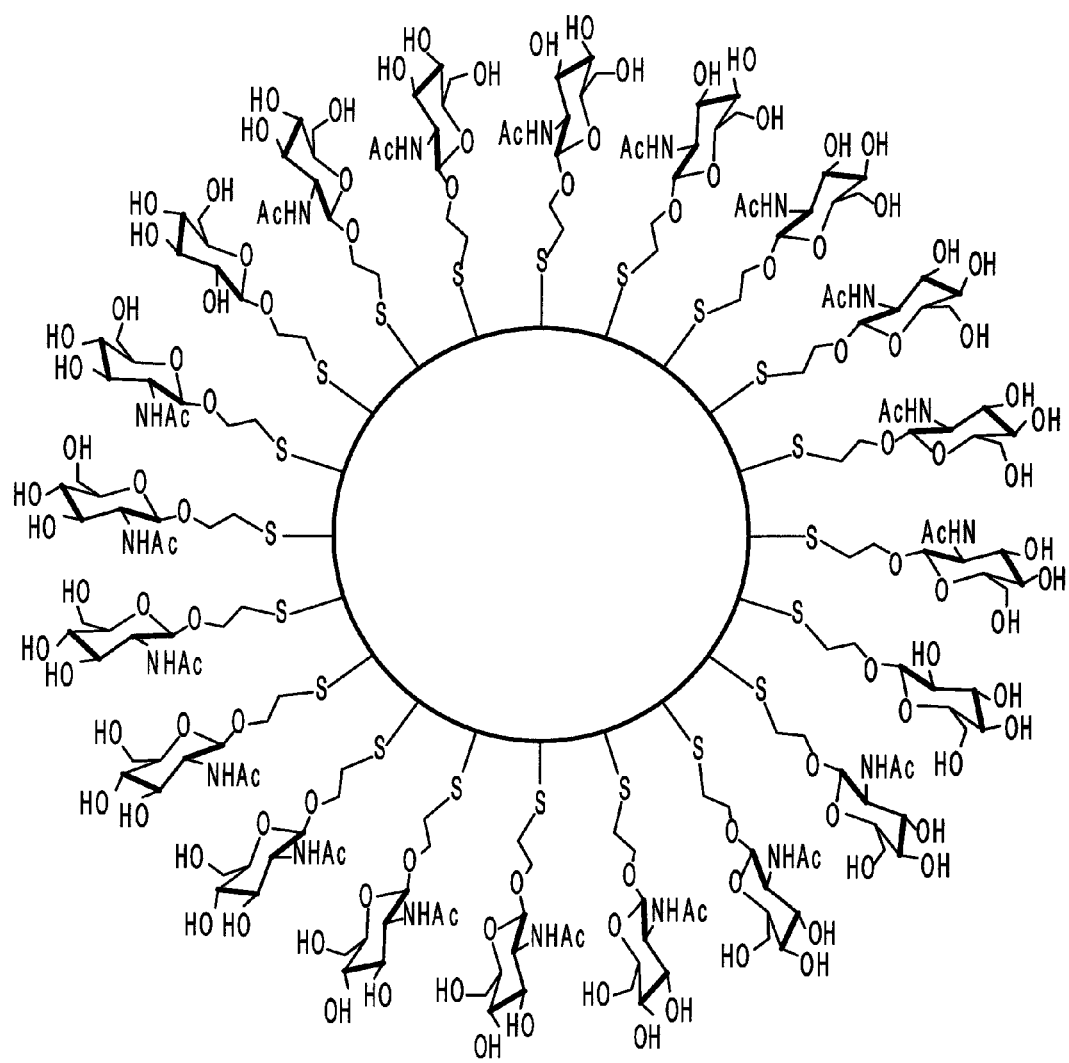
FIG. 4 shows a schematic representation of nanoparticles having a plurality of ligands in the ratio 1:9 of GlcC2:GlcNAc "NP-GlcC2(1)GlcNAc(9)"

Without wishing to be bound by any theory, a schematic representation of the resulting nanoparticles having a plurality of ligands in the ratio 1:9 of GlcC2:GlcNAc "NP-GlcC2 (1)GlaNAc(9)" is shown in FIG. 4.

NP-GlcC2(1)alpha-Gal(1)

To a solution of 1 (12 mg, 50 μmol) and 3 (12 mg, 50 μmol) in MeOH (8.3 mL) a 0.025M aqueous solution of HAuCl₄ (1.33 mL, 33 μmol) was added. The solution was shaken during 30 seconds and then an aqueous solution of NaBH₄ 1N (0.67 mL, 0.67 mmol) was added in several portions (134 μL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.). The process was repeated three times, washing with 2 mL of water. The residue was dissolved in 7 mL of water. An aliquot was freeze dried for quantitation. [NP]=0.7 mg/mL.

Figure 5:
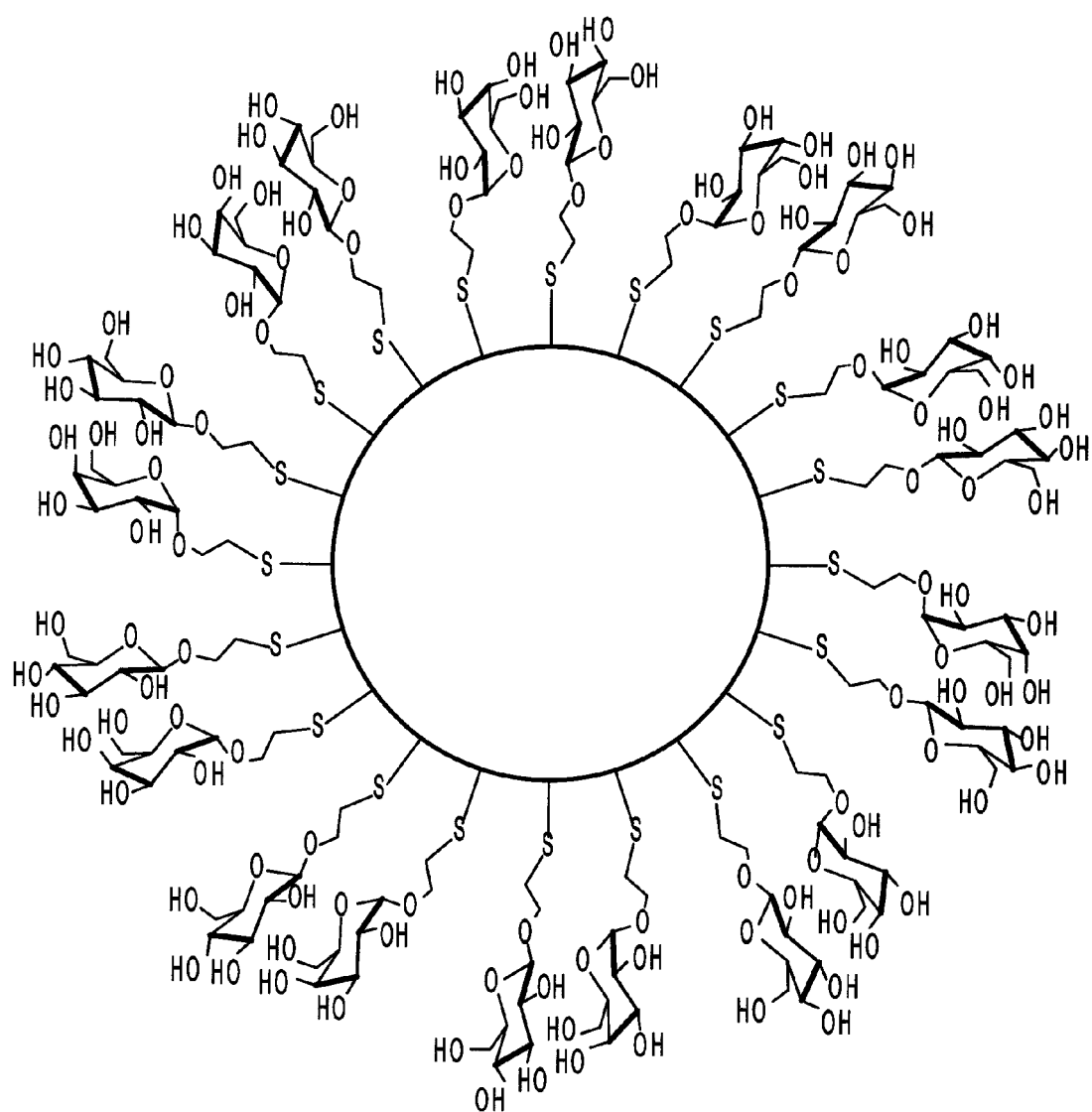
FIG. 5 shows a schematic representation of nanoparticles having a plurality of ligands in the ratio 1:1 of GlcC2:alpha-Gal "NP-GlcC2(1)alpha-Gal(1)"

Without wishing to be bound by any theory, a schematic representation of the resulting nanoparticles having a plurality of ligands in the ratio 1:1 of GlcC2:alpha-Gal "NP-GlcC2 (1)alpha-Gal(1)" is shown in FIG. 5.

NP-betaGlcC2(1)EG6NH2(1)

To a solution of 1 (12 mg, 50 µmol) and 6 (14.85 mg, 50 µmol) in MeOH (8.3 mL) a 0.025M aqueous solution of $HAuCl_4$ (1.33 mL, 33 µmol) was added. The solution was shaken during 30 seconds and then an aqueous solution of $NaBH_4$ 1N (0.67 mL, 0.67 mmol) was added in several portions (134 µL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.). The process was repeated three times, washing with 2 mL of water. The residue was dissolved in 7 mL of water. An aliquot was freeze dried for quantitation. [NP]=0.9 mg/mL.

Figure 6:
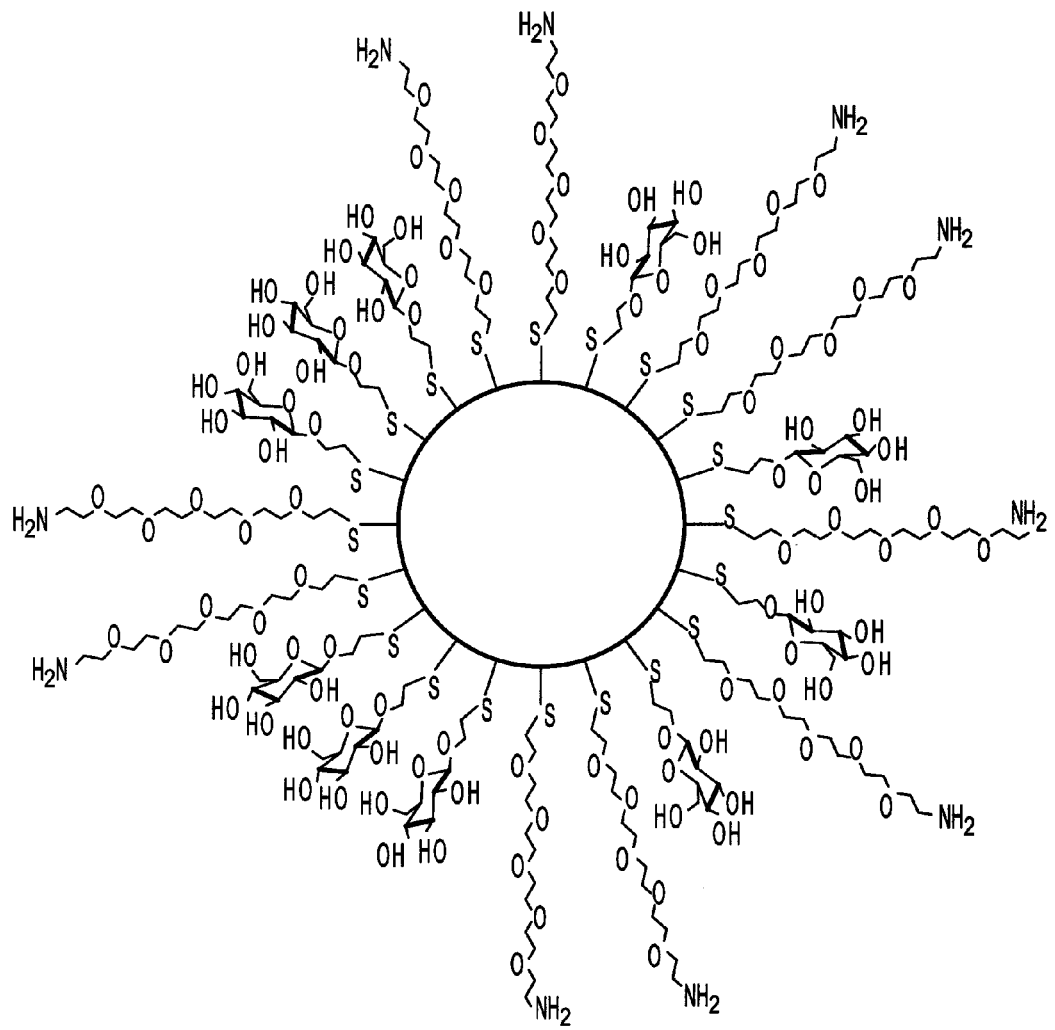
FIG. 6 shows a schematic representation of nanoparticles having a plurality of ligands in the ratio 1:1 of betaGlcC2:EG6NH2 "NP-betaGlcC2(1)EG6NH2(1)"

Without wishing to be bound by any theory, a schematic representation of the resulting nanoparticles having a plurality of ligands in the ratio 1:1 of betaGlcC2:EG6NH2 "NP-betaGlcC2(1)EG6NH2(1)" is shown in FIG. 6.

NP-GlcNHAc(1)EG6NH2(1)

To a solution of 2 (14 mg, 50 µmol) and 6 (14.85 mg, 50 µmol) in MeOH (8.3 mL) a 0.025M aqueous solution of $HAuCl_4$ (1.33 mL, 33 µmol) was added. The solution was shaken during 30 seconds and then an aqueous solution of $NaBH_4$ 1N (0.67 mL, 0.67 mmol) was added in several portions (134 µL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.).

The process was repeated three times, washing with 2 mL of water. The residue was dissolved in 6 mL of water. An aliquot was freeze dried for quantitation. [NP]=0.6 mg/mL.

Figure 7:
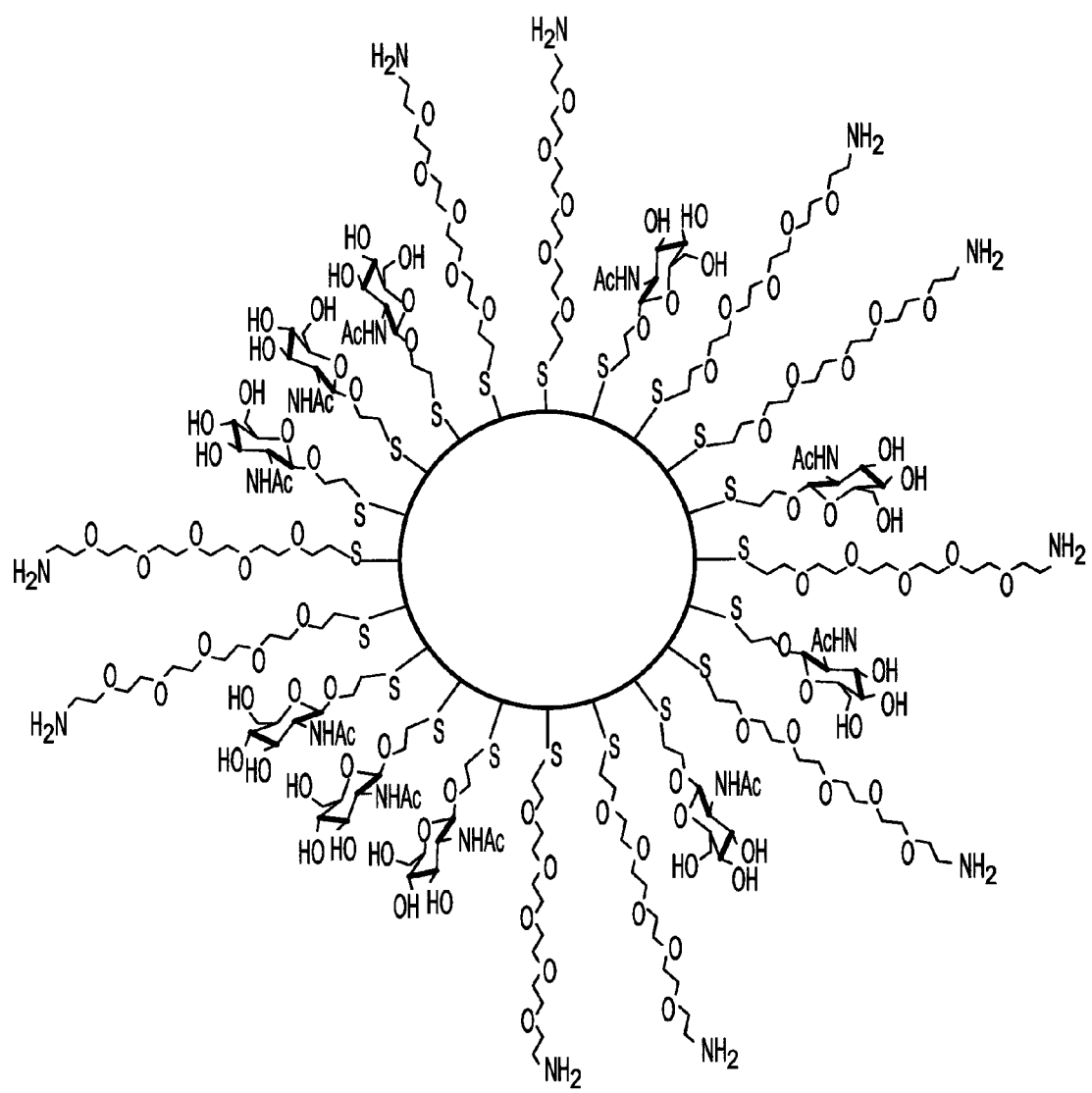
FIG. 7 shows a schematic representation of nanoparticles having a plurality of ligands in the ratio 1:1 of GlcNHAc:EG6NH2 "NP-GlcNHAc(1)EG6NH2(1)"

Without wishing to be bound by any theory, a schematic representation of the resulting nanoparticles having a plurality of ligands in the ratio 1:1 of GlcNHAc:EG6NH2 "NP-GlcNHAc(1)EG6NH2(1)" is shown in FIG. 7.

NP-alpha-Glc(1)EG6NH2(1)

To a solution of 4 (12 mg, 50 µmmol) and 6 (14.85 mg, 50 µmmol) in MeOH (8.3 mL) a 0.025M aqueous solution of $HAuCl_4$ (1.33 mL, 33 µmmol) was added. The solution was shaken during 30 seconds and then an aqueous solution of $NaBH_4$ 1N (0.67 mL, 0.67 mmol) was added in several portions (134 µL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.). The process was repeated three times, washing with 2 mL of water. The residue was dissolved in 4 mL of water. An aliquot was freeze dried for quantitation. [NP]=0.8 mg/mL.

Figure 8:
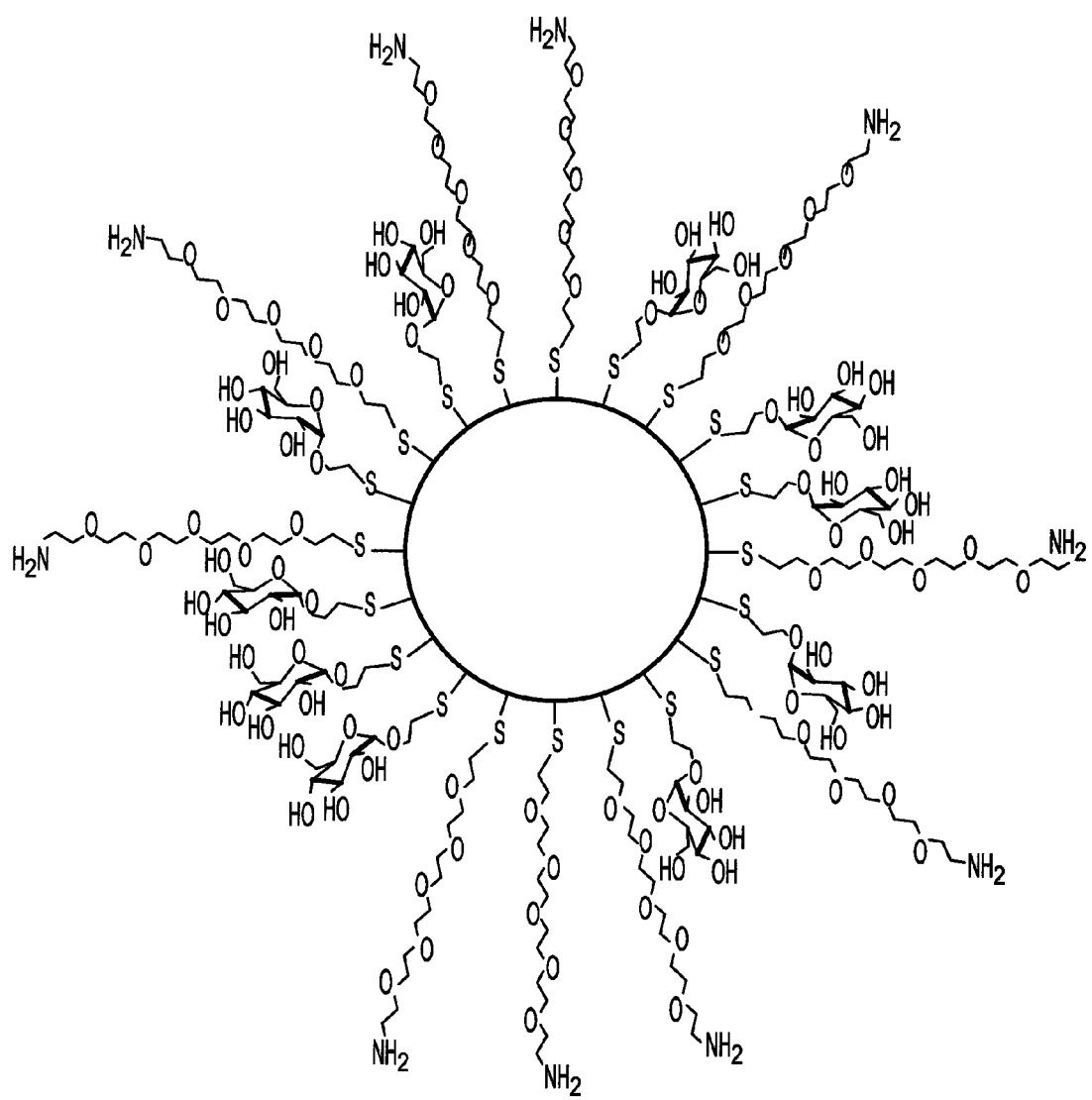
FIG. 8 shows a schematic representation of nanoparticles having a plurality of ligands in the ratio 1:1 of alpha-Glc:EG6NH2 "NP-alpha-Glc(1)EG6NH2(1)"

Without wishing to be bound by any theory, a schematic representation of the resulting nanoparticles having a plurality of ligands in the ratio 1:1 of alpha-Glc:EG6NH2 "NP-alpha-Glc(1)EG6NH2(1)" is shown in FIG. 8.

NP-alpha-Glc

To a solution of 4 (24 mg, 100 µmol) in MeOH (8.3 mL) a 0.025M aqueous solution of $HAuCl_4$ (1.33 mL, 33 µmol) was added. The solution was shaken during 30 seconds and then an aqueous solution of $NaBH_4$ 1N (0.67 mL, 0.67 mmol) was added in several portions (134 µL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.). The process was repeated three times, washing with 2 mL of water. The residue was dissolved in 5 mL of water. An aliquot was freeze dried for quantitation. [NP]=1.0 mg/mL.

Figure 9:
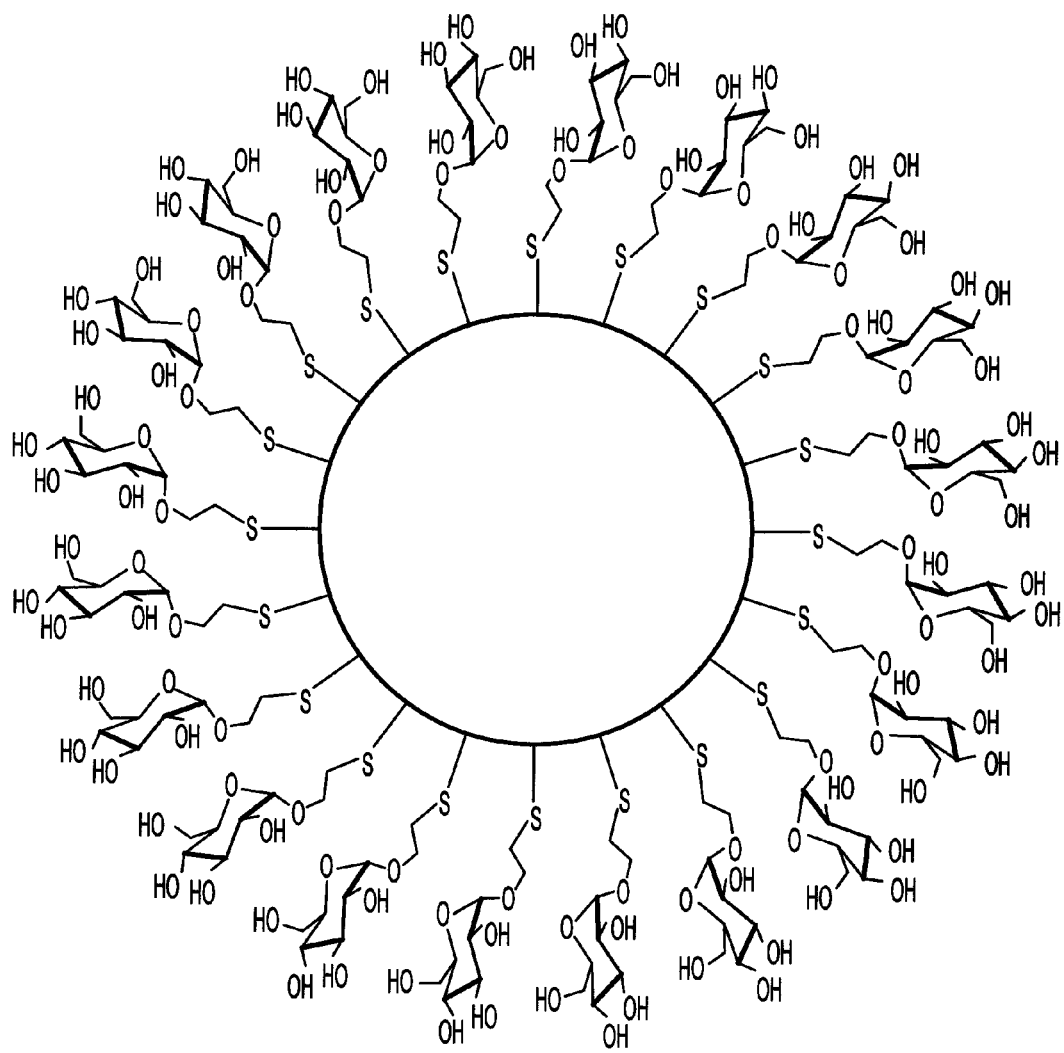
FIG. 9 shows a schematic representation of nanoparticles having a plurality of ligands of alpha-Glc "NP-alpha-Glc"

Without wishing to be bound by any theory, a schematic representation of the resulting nanoparticles having a plurality of ligands of alpha-Glc "NP-alpha-Glc" is shown in FIG. 9.

NP-GlcC2(1)GlcNH_IAA(1)

To a solution of 1 (12 mg, 50 µmol) and 5 (12 mg, 50 µmol) in MeOH (8.3 mL) a 0.025M aqueous solution of $HAuCl_4$ (1.33 mL, 33 µmol) was added. The solution was shaken during 30 seconds and then an aqueous solution of $NaBH_4$ 1N (0.67 mL, 0.67 mmol) was added in several portions (134 µL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.). The process was repeated three times, washing with 2 mL of water.

The residue was dissolved in 8 mL of 100 mM MES and treated with EDC (153 mg, 0.8 mmol) and imidazole-4-acetic acid monohydrochloride (81 mg, 0.5 mmol) for 14 hours. The mixture was and purified by centrifugal filtering (10 KDa AMICON 4 mL, 4500 g, 15 min, 15° C.). The process was repeated three times, washing with 2 mL of water. The residue was dissolved in 4 mL of water. An aliquot was freeze dried for quantitation. [NP]=0.9 mg/mL.

Figure 10:
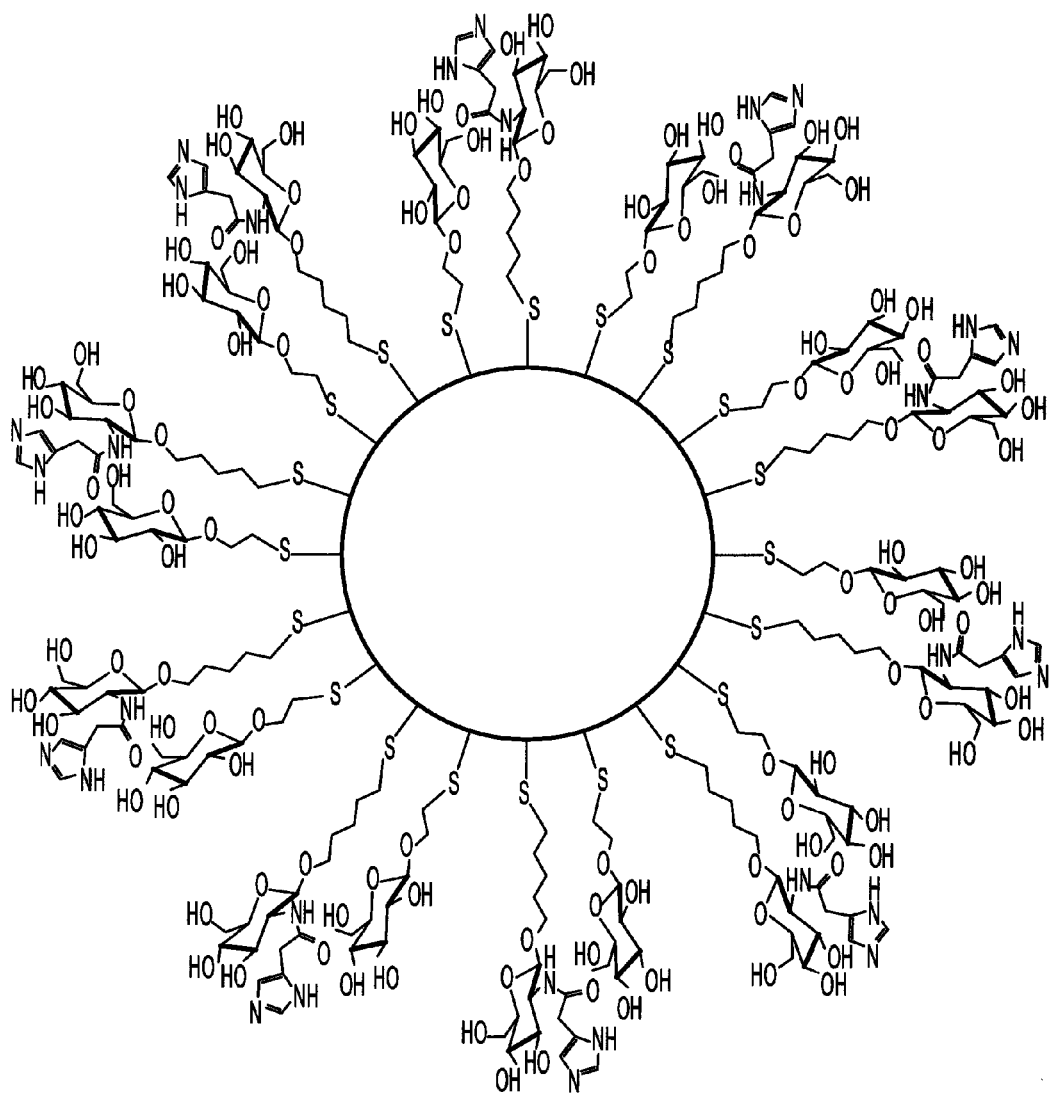
FIG. 10 shows a schematic representation of nanoparticles having a plurality of ligands in the ratio 1:1 of GlcC2:GlcNH_IAA "NP-GlcC2(1)GlcNH_IAA(1)"

Without wishing to be bound by any theory, a schematic representation of the resulting nanoparticles having a plurality of ligands in the ratio 1:1 of GlcC2:GlcNH_IAA "NP-GlcC2(1)GlcNH_IAA(1)" is shown in FIG. 10.

NP-alpha-Gal(1)EG6NH2(1)

Preparation of amine alpha-gal gold nanoparticles Batch MI-NP-10-AMINE-GAL: To a mix of amine-mercapto hexaethylenglycol linker 6 and alpha-galactose ligand 3 in a ratio 1:1 (0.58 mmol, 3 eq.) in MeOH (49 mL) was added an aqueous solution of gold salt (7.86 mL, 0.19 mmol, 0.025M). The reaction was stirred during 30 seconds and then, an aqueous solution of $NaBH_4$ (1N) was added in several portions (4.32 mL, 4.32 mmol). The reaction was shaken for 100 minutes at 900 rpm. After this time, the suspension was centrifuged 1 minute at 14000 rpm. The supernatant is removed and the precipitated was dissolved in 2 mL of water. Then, 2 mL of the suspension were introduced in two filters (AMICON, 10 KDa, 4 mL) and were centrifuged 5 minutes at 4500 g. The residue in the filter was washed twice more with water. The final residue was dissolved in 80 mL of water.

Figure 11:
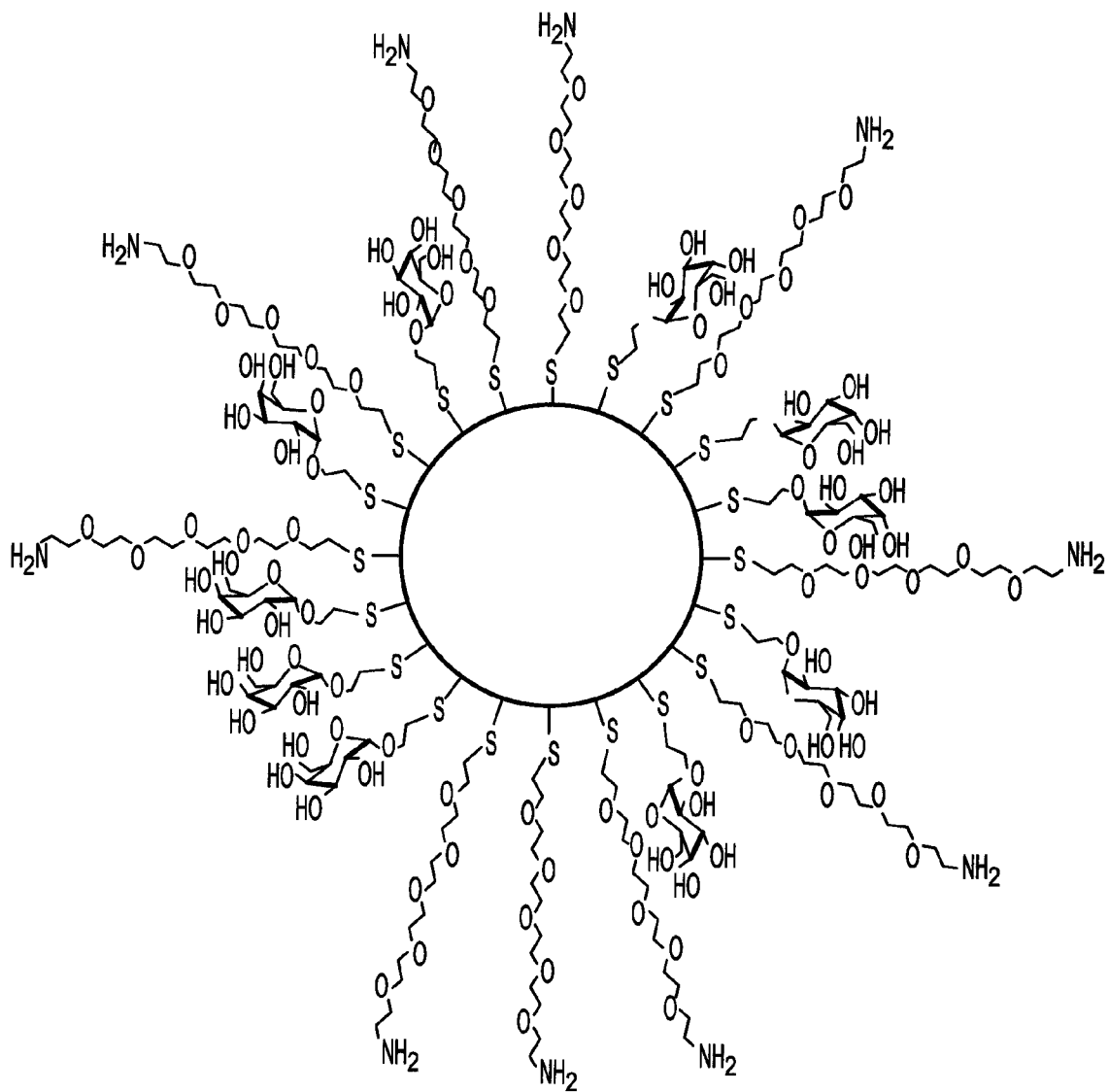
FIG. 11 shows a schematic representation of nanoparticles having a plurality of ligands in the ratio 1:1 of alpha-Gal.

Without wishing to be bound by any theory, a schematic representation of the resulting nanoparticles having a plurality of ligands in the ratio 1:1 of alpha-Gal:EG6NH2 "NP-alpha-Gal(1)EG6NH2(1)" is shown in FIG. 11.

For the preparation of gold NPs manufacture was under laminar flow cabinet. All glass and plastic material (such as eppendorfs, vials and bottles) and solvent (water, HAc) were first sterilized in an autoclave. All other disposables (such as tips and filters) came pre-sterilized.

Example 3

Insulin Binding to Nanoparticles

The following method details how the binding of insulin to alphaGal(1) EG6NH2(1) NPs was performed. The method used fixed insulin and variable NP levels, lower/different levels of NP were used for the other NP samples tested, but with this exception the method was the same for all NPs tested.

Preparation of insulin stock solution; weight 20 mg human insulin into a clean glass vial and add 8.7 ml 10 mM HCl mix gently insulin will dissolve completely, then pH back to 7.5 by adding 1.3 ml 100 mM Tris base, the solution will go cloudy briefly as the insulin passes through its isoelectric point, check the pH is 7.5 and store capped at 4° C., this is the 2 mg/ml insulin stock solution.

Add variable amounts of alphaGal(1) EG6NH2(1) NPs to an eppendorf or suitably sized vessel, for example; 15, 30, 60, 120, 240 and 480 nmoles gold content of NP, make up to a total volume of 200 µl with water, then add 50 µl of human insulin (2 mg/ml in tris HCl pH7.5—see above for preparation of insulin stock solution). Mix gently and leave at room temp for 2 h, follow with a 2 minute bench spin (2000 rpm) to bring down the aggregate. A standard tube which has just 200 µl water and 50 µl insulin should be performed to give the maximum supernatant value, as should a blank i.e. 50 µl Tris HCl pH7.5+200 µl water. If high accuracy is required a sample containing a known amount of alphaGal(1) EG6NH2 (1) NP i.e. 10 µg gold content is made up to 200 µl with water, and 50 µl of the insulin buffer added (Tris HCl pH7.5), this can be used to correct for the slight positive result the alphaGal(1) EG6NH2(1) NP gives in the BCA assay see below*.

Assay the supernatants, 20 µl in triplicate by standard micro BCA assay (Pierce kit 23235), this will give data showing how much insulin remains in supernatant. By subtracting this value from the value for the insulin only standard calculate the amount of NP bound insulin, it can also be expressed as a percent if required. The data obtained here shows the amount of alphaGal(1) EG6NH2(1)-NP that if required to maximally bind the 100 µg of insulin used, these conditions can be scaled up to produce the amount alphaGal(1) EG6NH2 (1)-NP-insulin required.

*The data can be correcting for the slight interference of the free alphaGal(1) EG6NH2(1)-NP in the BCA assay. To do this perform a gold analysis on all the final samples and calculate how much gold remains in the various supernatants, higher levels will be seen in samples with an excess of NP to insulin. Use the BCA value for the 10 µg gold content NP to correct relative to the gold content seen, as demonstrated by the following example:

If the 10 µg gold content NP without insulin gives 0.5 by BCA and 40 µg Au test NP supernatant gives BCA of 1.25, and also shows gold content of 5 µg, that means 0.25 of BCA value (50% of 0.5) is actually due to the free NP, hence corrected value for 40 µg gold test NP supernatant should be 1.00 not 1.25. This is a simplified, illustrative example, the correction factor will be minimal where the gold content in the supernatant is low.

The amount of human insulin bound (in nmoles) per amount of gold (in nmoles) is shown in FIG. 12, wherein:
Glc=2'-thioethyl-β-D-glucopyranoside;
GlcNAc=2'-thioethyl-2-acetamido-2-deoxy-β-D-glucopyranoside;
GlcamineIAA=5'-thiopentanyl-2-deoxy-2-imidazolacetamido-α,β-D-glucopyranoside (alpha, beta mix of isomers);
AGal=2'-thioethyl-α-D-galactopyranoside;
EG6NH2=1-amino-17-mercapto-3,6,9,12,15,-pentaoxaheptadecanol;
AGlc=2'-thioethyl-α-D-glucopyranoside; and
The numbers in the legend refer to the ligand stiochiometry.

As can be seen by reference to FIG. 12, a relatively high degree of insulin binding was obtained using nanoparticles having a corona of AGal and EG6NH2 in approximately 1:1 ratio. Insulin binding was also exhibited by nanoparticles having any of the following corona compositions:
AGal: EG6NH2 1:1 (Trace 11 FIG. 12)
Glc:GlcamineIAA 1:1 (Trace 10 FIG. 12)
AGlc: EG6NH2 1:1 (Trace 8 FIG. 12)
BGlc: EG6NH2 1:1 (Trace 6 FIG. 12)
GlcNAc: EG6NH2 1:1 (Trace 7 FIG. 12).

The insulin bound to nanoparticles as described herein was found to be releasable upon contact with a physiological solution (e.g. a saline solution) and was found to be detectable such that a positive result was achieved in an ELISA for (human) insulin. These results indicate that insulin-bound nanoparticles of the invention provide insulin in a form that is available for interaction with biological systems and/or components. Thus, the nanoparticles are capable of acting as a carrier/stabiliser of insulin (e.g. for storage and/or processing for incorporation into, e.g., a pharmaceutical product) whilst also maintaining the ability to present or make available insulin (for example, monomeric insulin) to exert its biological effects, for example following delivery to a subject, organ or cell thereof.

Example 4

Characterisation of Nanoparticles

I) Characterization of Insulin Gold Nanoparticles Batch MI-NP-10-Ins (NP-alpha-Gal(1)EG6NH2(1))
a) Gold content: The gold content was determined using a method based on the formation of a coloured complex between ethopropazine and the gold after complete oxidation to Au (III). The absorbance of the sample is measured at 513 nm and quantitatively compared to similar solutions having a known amount of gold.

The gold content was determined to be (batch #NP10): 262.5±56.3 mg/L.

TEM: a transmission electron microscopy (TEM) image of the nanoparticle suspension is shown in FIG. 13.

The sample was determined to have the following size characteristics for the gold core:
Count=783
Mean (diameter)=2.323 nm±0.716 nm
Min.=1.002 nm
Max.=4.859 nm
Mode=2.104 nm d) Size distribution by Dynamic Light Scattering: number and volume distributions were determined by dynamic light scattering (DLS) for MI-NP-10 amine-gal (i.e. NP-alpha-Gal (1)EG6NH2(1) nanoparticles), and are shown in FIGS. 14 A and B, respectively.

Figure 14A:
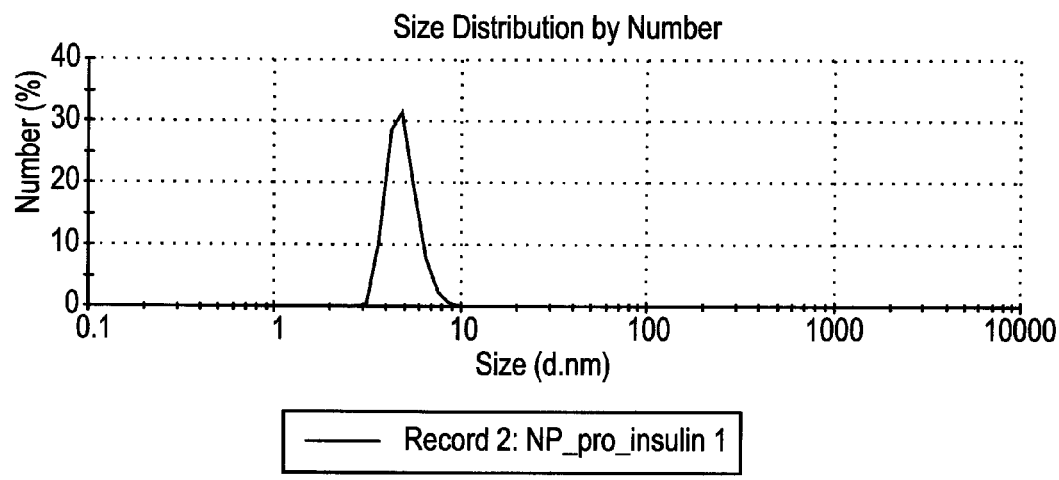

The peak value for the peak shown in FIG. 14A is as follows:
Peak 1 4.875 nm

Figure 14B:
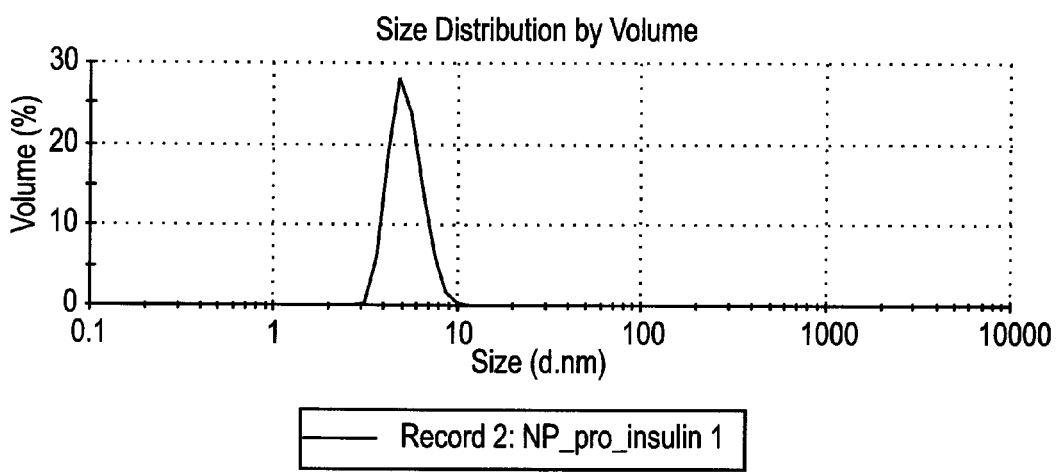

The peak value for the peak shown in FIG. 14B is as follows:
Peak 1 5.289 nm

III) Final Preparation of Insulin Gold Nanoparticles Batch MI-NP-10-INS.

A solution of gold nanoparticles MI-NP-10 (13.041 mg gold) was made up to 49.68 mL of water. To the final solution was added acetic acid to obtain a pH=4.6. Then, 55.7 mg of human insulin in 27.85 mL of Tris.HCl pH 7.5 was added. The suspension was left 24 hours and after this time, was centrifuged 1 minute at 4500 g. The supernatant was removed and stored for further insulin and gold content analysis. The precipitate was resuspended in 3.220 mL of water to get a final insulin concentration of 500 units insulin/mL.

The size distribution of the insulin-gold nanoparticles was determined by DLS analysis. The insulin content was determined by BCA standard assay.

** The final preparation of insulin gold NP was manufactured under laminar flow cabinet. All glass and plastic material (such as eppendorfs and bottles) and solvent (such as water, TrisHCl and HAc) used were sterilized in an autoclave. All other disposables (such as tips and filters) came pre-sterilized.

Characterisation:

a) Size distribution by Dynamic Light Scattering is shown by number and volume in FIG. 15 A, and B, respectively for MI-NP-10-INS (amine-gal-INSULIN nanoparticles).

Figure 15A:
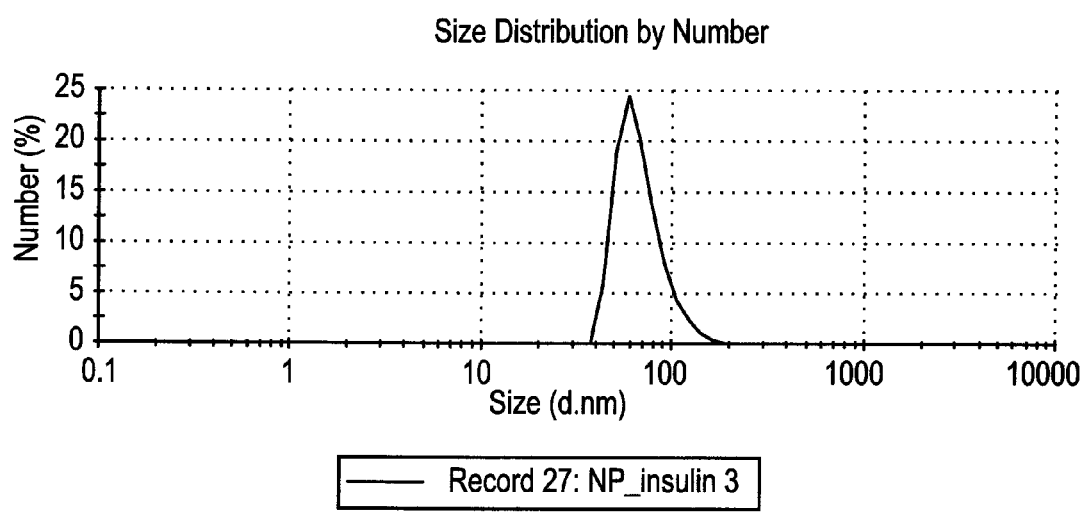

The peak value for the peak shown in FIG. 15A is as follows:

Peak 1 68.46 nm

Figure 15B:
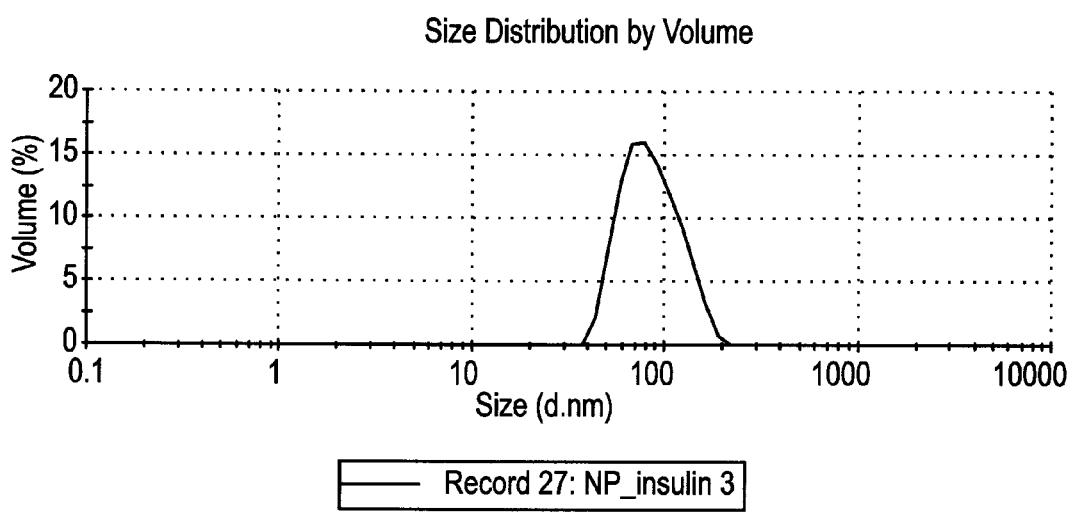

The peak value for the peak shown in FIG. 15B is as follows:

Peak 1 88.38 nm b) Insulin content:

The % of insulin binding to the nanoparticles was determined by the following formula:

$$\% \text{ insulin} = \frac{\text{insulin added} - \text{insulin supernatant}}{\text{insulin added}} \times 100$$

TABLE 2

| | Insulin content | | | |
|---|---|---|---|---|
| Sample | Insulin added (mg) | Insulin supernatant (mg) | Insulin bound (mg) | % insulin bound |
| MI-NP-10 insulin | 55.700 | 1.308 | 54.4 | 97.65 |

Concentration of Insulin and Gold in NP-Insulin Nanoparticles:

Insulin: 55.7 mg Insulin
Gold: 13.041 mg of gold
Total volume: 3.23 mL water
Final insulin concentration: 17.25 mg insulin/mL=500 units/mL
Final gold concentration: 4.037 mg Au/mL.

Without wishing to be bound by any theory, the present inventors consider the following:

102 Au atoms/NP, for which the mathematical result is 14 insulin molecules attached to 1 NP. Since geometrical considerations allow space for about 7 insulin molecules on the surface of the nanoparticle, these results suggest that each NP contains 7 insulin dimer units.

Further characterisation of the insulin gold nanoparticles Batch MI-NP-10-INS yielded the following results.

Final insulin concentration: 17.25 mg insulin/mL=500 U/mL, determined by colorimetric bicinchonicic acid assay after calibration against insulin standardized solutions of known concentrations.

Final gold concentration: 4.037 mg Au/mL, determined by colorimetric assay with ethopropazine assay after calibration against gold standardized solutions of known concentrations.

Total volume: 3.23 mL in MilliQ water.

After geometrical considerations, one α-galactose-EG-amine-Au nanoparticle contains a gold core with 102 atoms. Then:

4.037 mg=2.049e-5 moles=1.234e19 atoms=1.21e17 nanoparticles 17.25 mg=2.97e-6 moles=1.789e18 molecules Therefore one α-galactose-EG6NH2-Au nanoparticle is bound to about between 14 and 15 insulin molecules to produce the final nanoparticle.

Results from Thermogravimetric Analysis:

Without wishing to be bound by any theory, the present inventors consider that for insulin-NP we have 500 ug of dry weight in which 410 ug is decomposed. Therefore the percent organic is 82%. Considering 102 atoms of gold in one α-galactose-EG6NH2-Au nanoparticle, gold weight would be 20091(18%) and an organic corona 12122. Therefore to have a particle that is 82% organic it must have weight of 111616 that is 91525 organic. Since 12122 of organic is corona that leaves about 79403 of the organic as insulin. Since insulin has MW 5808 then we must have 14 moles insulin per particle.

FIG. 16 shows the experimental thermogravimetric analysis (TGA) data.

Example 5

Zn Optimisation of Insulin Binding

Gold nanoparticles (NPs), alphaGal(1) EG6NR2(1) NPs, were prepared as described in Example 2 above. In order to evaluate the influence of Zn on insulin binding to the NPs, a first batch of NPs was synthesised in the absence of Zn. A second batch of NPs was synthesised in the presence of 1.33 equivalents of Zn. A third batch of NPs was synthesised in the absence of Zn, but had 1.33 equivalents of $ZnCl_2$ added to the NPs post-synthesis. The binding of human insulin to the three batches of gold NPs was then measured.

The results are shown in FIG. 17. FIG. 17 displays a Graph showing the amount of fixed 17.2 nmoles of Insulin binding to varying gold NP concentrations. Comparison of NP synthesised without Zn, a NP with synthesised with 1.33 eq, and Zn free NPs with 1.33 eq of ZnCl2.

The graph in FIG. 17 shows that with no zinc present insulin binding is at a very low level. When zinc is present insulin binding is significantly higher up to quantitative. Equivalent insulin binding occurs whether the zinc is present during NP synthesis or whether it is added post synthesis.

Without wishing to be bound by any theory, the present inventors believe that the $Zn^{2+}$ cation provides improved insulin binding to the gold NPs. Other forms of Zn, such as ZnO may also mediate improved insulin binding. In particular, presence of ZnO in gold NP sample that had been stored for a period of months indicates that ZnO can form and may additionally or alternatively to $Zn^{2+}$ cation mediate or facilitate improved insulin binding to the NPs.

The importance of $Zn^{2+}$ in insulin crystallisation, form and function has been reported previously. However, data described herein indicate that insulin bound to NPs, including in the presence of $Zn^{2+}$, is in monomeric or dimeric form rather than the hexameric form more commonly associated with human insulin in the presence of $Zn^{2+}$ (i.e. insulin not bound to NPs). This may present a considerable advantage in relation to the present invention because monomeric or dimeric insulin is preferred in many settings (e.g. clinical settings) as compared with hexameric insulin.

The present inventors have found that binding of GLP-1 to gold NPs (described herein) takes place the presence of Zn (including, but not limited to $Ze^{2+}$ and/or ZnO). GLP-1 binding to gold NPs described herein was to NPs synthesised in the presence of Zn. It is specifically contemplated herein that Zn may be present in GLP-1-bound gold nanoparticle compositions.

Example 6

GLP-1 Binding to Gold Nanoparticles

Gold nanoparticles (NPs), alphaGal(1) EG6NH2(1) NPs, were prepared as described in Example 2 above. Rather than adding insulin, GLP-1 was added. It was found that GLP-1 binds to the NPs. The binding of a fixed 29.8 nmoles of GLP-1 to varying gold NP concentrations is shown in FIG. 18. These results demonstrate that a peptide other than insulin binds to the nanoparticles of the invention.

Example 7

Nanoparticles Co-Binding More than One Protein: Mixed Insulin/GLP-1 Nanoparticles Gold nanoparticles (NPs), alphaGal(1) EG6NH2(1) NPs, were prepared as described in Example 2 above. Insulin and GLP-1 were both added to the NPs. An aqueous solution of the GLP-1/Insulin NPs was subjected to analysis by MALDI and the results are shown in FIG. 19. The GLP-1/Insulin NPs were subjected to HPLC and the trace is shown in FIG. 20. The HPLC data show that 19.8 mg of insulin was measured and 1.33 mg of GLP-1.

The binding reaction was performed using a mixture of 26.2 mg insulin and 1.8 mg GLP-1. The HPLC data show that the approximate ratio of insulin:GLP-1 is maintained on binding to the nanoparticles.

The MALDI and HPLC data demonstrate the mixed binding of GLP-1 and Insulin to gold nanoparticles. Without wishing to be bound by any theory, the present inventors believe that co-binding of two or more different species of peptide to the nanoparticle of the invention may be preferred in certain settings (e.g. certain clinical settings) as compared with binding of a single species of peptide. In particular, combinations of peptides may be carried on a nanoparticle such that the peptides perform mutually beneficial functions and/or act in concert, such as in a synergistic fashion.

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Any sub-titles herein are included for convenience only, and are not to be construed as limiting the disclosure in any way.

The invention claimed is:

1. A nanoparticle comprising:
   (i) a core comprising a metal;
   (ii) a corona comprising a plurality of ligands covalently linked to the core, wherein at least one of said ligands comprises a carbohydrate moiety; and
   (iii) at least one peptide or polypeptide non-covalently bound to the corona.

2. The nanoparticle according to claim 1, wherein the peptide or polypeptide is reversibly bound to the corona.

3. The nanoparticle according to claim 1, wherein the peptide or polypeptide is bound to the corona such that at least a fraction of the bound peptide or polypeptide is released from the nanoparticle upon contacting the nanoparticle with a physiological solution.

4. The nanoparticle according to claim 1, wherein the peptide or polypeptide is capable of stimulating a physiological response in a mammalian subject.

5. The nanoparticle according to claim 4, wherein the peptide or polypeptide is capable of stimulating a reduction in blood glucose levels in a mammalian subject.

6. The nanoparticle according to claim 1, wherein the peptide or polypeptide is selected from the group consisting of: insulin, GLP-1, IGF1, IGF2, relaxin, INSL5, INSL6, INSL7, pancreatic polypeptide(PP), peptide tyrosine tyrosine (PTT), neuropeptide Y, oxytocin, vasopressin, GnRH, TRH, CRH, GHRH/somatostatin, FSH, LH, TSH, CGA, prolactin, CIIP, ACTH, MSH, enorphins, lipotropin, GH, calcitonin, PTH, inhibin, relaxin, hCG, HPL, glucagons, insulin, somatostatin, melatonin, thymosin, thmulin, gastrin, ghrelin, thymopoietin, CCK, GIP secretin, motin VIP, enteroglucagon, IGF-1, IGF-2, leptin, adiponectin, resistin Osteocalcin, renin, EPO, calicitrol, ANP, BNP, chemokines, cytokines, and adipokines.

7. The nanoparticle according to claim 6, wherein the polypeptide is monomeric and/or dimeric human insulin.

8. The nanoparticle according to claim 1, wherein the carbohydrate moiety comprises a monosaccharide and/or a disaccharide.

9. The nanoparticle according to claim 8, wherein the carbohydrate moiety comprises a glycoside of galactose, glucose, glucosamine, N-acetylglucosamine, mannose, fucose and/or lactose.

10. The nanoparticle according to claim 9, wherein the carbohydrate moiety comprises a galactopyranoside and/or a glucopyranoside.

11. The nanoparticle according to claim 1, wherein the carbohydrate moiety is covalently linked to the core via a linker selected from the group consisting of: sulphur-containing linkers, amino-containing linkers, phosphate-containing linkers and oxygen-containing linkers.

12. The nanoparticle according to claim 11, wherein the linker comprises an alkyl chain of at least two carbons.

13. The nanoparticle according to claim 1, wherein said at least one ligand comprising a carbohydrate moiety is selected from the group consisting of: 2'-thioethyl-α-D-galactopyranoside, 2'-thioethyl-β-D-glucopyranoside, 2'-thioethyl-2-acetamido-2-deoxy-β-D-glucopyranoside, 5'-thiopentanyl-2-deoxy-2-imidazolacetamido-α,β-D-glucopyranoside and 2'-thioethyl-α-D-glucopyranoside, and wherein said at least one ligand comprising a carbohydrate moiety is covalently linked to the core via its sulphur atom.

14. The nanoparticle according to claim 1, wherein said plurality of ligands covalently linked to the core comprises at least a first ligand and a second ligand, wherein the first and second ligands are different.

15. The nanoparticle according to claim 14, wherein:
   (a) said first ligand comprises 2'-thioethyl-α-D-galactopyranoside and said second ligand comprises 1-amino-17-mercapto-3,6,9,12,15,-pentaoxa-heptadecanol;
   (b) said first ligand comprises 2'-thioethyl-β-D-glucopyranoside or 2'-thioethyl-α-D-glucopyranoside and said second ligand comprises 5'-thiopentanyl-2-deoxy-2-imidazolacetamido-α,β-D-glucopyranoside;
   (c) said first ligand comprises 2'-thioethyl-β-D-glucopyranoside or 2'-thioethyl-α-D-glucopyranoside and said second ligand comprises 1-amino-17-mercapto-3,6,9,12,15,-pentaoxa-heptadecanol; or
   (d) said first ligand comprises 2'-thioethyl-2-acetamido-2-deoxy-β-D-glucopyranoside and said second ligand comprises 1-amino-17-mercapto-3,6,9,12,15,-pentaoxa-heptadecanol, and wherein said first and second ligands are covalently linked to the core via their respective sulphur atoms.

16. The nanoparticle according to claim 14, wherein said first ligand comprises a carbohydrate moiety and said second ligand is a non-carbohydrate ligand.

17. The nanoparticle according to claim 16, wherein said second ligand comprises an amine group.

18. The nanoparticle according to claim 17, wherein said second ligand comprises 1-amino-17-mercapto-3,6,9,12,15,-pentaoxa-heptadecanol covalently linked to the core via its sulphur atom.

19. The nanoparticle according to claim 14, wherein said first ligand and said second ligand are present on the nanoparticle in a ratio of 1:40 to 40:1.

20. The nanoparticle according to claim 19, wherein the ratio is 1:10 to 10:1.

21. The nanoparticle according to claim 20, wherein the ratio is 1:2 to 2:1.

22. The nanoparticle according to claim 1, wherein the corona comprises at least 5 ligands per core.

23. The nanoparticle according to claim 22, wherein the corona comprises between about 10 to about 1000 ligands per core.

24. The nanoparticle according to claim 23, wherein the corona comprises 44-106 ligands per core.

25. The nanoparticle according to claim 1, wherein at least 5 or more peptide or polypeptide molecules are bound per core.

26. The nanoparticle according to claim 1, wherein the core comprises a metal selected from the group consisting of: Au, Ag, Cu, Pt, Pd, Fe, Co, Cd, Gd, Zn or any combination thereof.

27. The nanoparticle according to claim 26, wherein the core comprises a passive metal selected from the group consisting of: Au, Ag, Pt, Pd and Cu, or any combination thereof.

28. The nanoparticle according to claim 26, wherein the core comprises a combination of metals selected from the group consisting of: Au/Fe, Au/Ag, Au/Cu, Au/Ag/Cu, Au/Pt, Au/Pd, Au/Ag/Cu/Pd, Au/Gd, Au/Fe/Cu, Au/Fe/Gd, Au/Fe/Cu/Gd.

29. The nanoparticle according to claim 1, wherein the core is magnetic.

30. The nanoparticle according to claim 1, wherein the core further comprises an NMR active atom selected from the group consisting of: $Mn^{2+}$, $Gd^{3+}$, $Eu^{2+}$, $Cu^{2+}$, $V^{2+}$, $Co^{2+}$, $Ni^{2+}$, $Fe^{2+}$, $Fe^{3+}$ and lanthanides$^{3+}$.

31. The nanoparticle according to claim 1, wherein the core further comprises a semiconductor.

32. The nanoparticle according to claim 31, wherein the semiconductor is selected from the group consisting of: cadmium selenide, cadmium sulphide, cadmium tellurium and zinc sulphide.

33. The nanoparticle according to claim 1, wherein the core comprises a metal oxide coated with a metal selected from the group consisting of: Au, Ag, Cu, Pt, Pd and Zn, or any combination thereof.

34. The nanoparticle according to claim 33, wherein said metal oxide is of the formula $XFe_2O_4$, where X is a metal selected from the group consisting of: Fe, Mn and Co.

35. The nanoparticle according to claim 1, wherein the nanoparticle core has a diameter in the range of about 0.5 nm to about 50 nm.

36. The nanoparticle according to claim 35, wherein said diameter is in the range of about 1 nm to about 10 nm, or is in the range of about 1.5 nm to about 2 nm.

37. The nanoparticle according to claim 1, wherein the nanoparticle comprises a divalent component.

38. The nanoparticle according to claim 37, wherein said divalent component is present in the corona of the nanoparticle.

39. The nanoparticle according to claim 37, wherein said divalent component is selected from the group consisting of divalent metals, divalent metal compounds or other component having a divalent state.

40. The nanoparticles according to claim 37, wherein said divalent component is selected from the group consisting of zinc, magnesium, copper, nickel, cobalt, cadmium, or calcium, and oxides and salts thereof.

41. The nanoparticle according to claim 40, wherein said zinc is selected from: $Zn^{2+}$ and ZnO.

42. The nanoparticle according to claim 41, wherein the zinc comprises $ZnCl_2$.

43. The nanoparticle according to claim 37, wherein said divalent component is present in an amount sufficient to produce a stabilizing effect and/or sufficient to enhance binding of the peptide or polypeptide to the corona relative to the level of binding of the peptide or polypeptide to the corona in the absence of the divalent component.

44. The nanoparticle according to claim 43, wherein said divalent component is present in an amount of about 0.5 to about 2.0 equivalents of said metal in said core.

45. The nanoparticle according to claim 43, wherein said divalent component is present in an amount of about 0.75 to about 1.5 equivalents of said metal in said core.

46. The nanoparticle according to claim 1, wherein the at least one peptide comprises GLP-1.

47. The nanoparticle according to claim 1, wherein the nanoparticle comprises at least two different species of peptide or polypeptide bound to the corona.

48. The nanoparticle according to claim 47, wherein said at least two different species of peptide or polypeptide comprise insulin and GLP-1.

49. A plurality of nanoparticles as defined in claim 1.

50. The plurality of nanoparticles according to claim 49, wherein the nanoparticle cores have an average diameter in the range of about 0.5 nm to about 50 nm.

51. The plurality of nanoparticles according to claim 50, wherein said average diameter is in the range of about 1 nm to about 10 nm, or is in the range of about 1.5 nm to about 2 nm.

52. A pharmaceutical composition comprising a plurality of nanoparticles according to claim 1 and one or more pharmaceutically acceptable carriers or excipients.

53. A pharmaceutical composition according to claim 52, wherein the composition is formulated for administration to a mammalian subject by intraveneous (i.v.), intramuscular (i.m.), intradermal (i.d.) or subcutaneous (s.c.) route.

54. A method of lowering blood glucose in a mammalian subject in need thereof, comprising administering a therapeutically effective amount of a nanoparticle as defined in claim 1 to said subject.

55. A method according to claim 54, wherein said administering comprises administering intravenously (i.v.), intramuscularly (i.m.), intradermally (i.d.) or subcutaneously (s.c.).

56. A method of treating diabetes in a mammalian subject in need thereof, comprising administering a therapeutically effective amount of a nanoparticle as defined in claim 1 to said subject.

57. An article of manufacture comprising:
at least one nanoparticle as defined in claim 1;
a container for housing the at least one nanoparticle; and
an insert and/or a label.

58. A method for forming mesoscopic peptide, polypeptide or protein clusters, said clusters having embedded therein one or more nanoparticles as defined in claim 1, said method comprising contacting said peptide, polypeptide or protein with said one or more nanoparticles at an ambient temperature.

59. A method according to claim 58, wherein the ambient temperature is between 15° C. and 30° C. or between 20° C. and 25° C.

60. A method for dissociating one or more clusters, said one or more clusters comprising a cluster of mesoscopic peptide, polypeptide or protein having embedded therein one or more nanoparticles as defined in claim 1, said method comprising subjecting said clusters to a temperature from 35° C. to the melting temperature (Tm) of the peptide, polypeptide or protein thereby causing said one or more clusters to dissociate into individual nanoparticle-peptide flocculants, nanoparticle-polypeptide flocculants or nanoparticle-protein flocculants.

61. A method for releasing monomeric peptides from one or more nanoparticle-peptide flocculants in a solution, said method comprising increasing the ionic strength of the solvent, wherein said nanoparticle-peptide flocculants comprise one or more nanoparticles as defined in claim 1.

62. A method according to claim 61, wherein the method comprises dissolution of said one or more nanoparticle-peptide flocculants in plasma, interstitial fluid or saliva.

63. A nanoparticle comprising:
(i) a core comprising a metal;
(ii) a corona comprising a plurality of ligands covalently linked to the core, which plurality of ligands comprises at least a first ligand and a second ligand, wherein:
(a) said first ligand comprises 2'-thioethyl-α-D-galactopyranoside and said second ligand comprises 1-amino-17-mercapto-3,6,9,12,15,-pentaoxa-heptadecanol;
(b) said first ligand comprises 2'-thioethyl-β-D-glucopyranoside or 2'-thioethyl-α-D-glucopyranoside and said second ligand comprises 5'-thiopentanyl-2-deoxy-2-imidazolacetamido-α,β-D-glucopyranoside;
(c) said first ligand comprises 2'-thioethyl-β-D-glucopyranoside or 2'-thioethyl-α-D-glucopyranoside and said second ligand comprises 1-amino-17-mercapto-3,6,9,12,15,-pentaoxa-heptadecanol; or (d) said first ligand comprises 2'-thioethyl-2-acetamido-2-deoxy-β-D-glucopyranoside and said second ligand comprises 1-amino-17-mercapto-3,6,9,12,15,-pentaoxa-heptadecanol,
and wherein said first and second ligands are covalently linked to the core via their respective sulphur atoms.

64. The nanoparticle according to claim 63, wherein said first ligand and said second ligand are present on the nanoparticle in a ratio of 1:40 to 40:1.

65. The nanoparticle according to claim 64, wherein the ratio is 1:10 to 10:1.

66. The nanoparticle according to claim 65, wherein the ratio is 1:2 to 2:1.

67. The nanoparticle according to claim 63, wherein the corona comprises at least 5 ligands per core.

68. The nanoparticle according to claim 67, wherein the corona comprises between about 10 to about 1000 ligands per core.

69. The nanoparticle according to claim 68, wherein the corona comprises 44-106 ligands per core.

70. The nanoparticle according to claim 63, wherein the core comprises a metal selected from the group consisting of: Au, Ag, Cu, Pt, Pd, Fe, Co, Cd, Gd, Zn or any combination thereof.

71. The nanoparticle according to claim 70, wherein the core comprises a passive metal selected from the group consisting of: Au, Ag, Pt, Pd and Cu, or any combination thereof.

72. The nanoparticle according to claim 70, wherein the core comprises a combination of metals selected from the group consisting of: Au/Fe, Au/Ag, Au/Cu, Au/Ag/Cu, Au/Pt, Au/Pd, Au/Ag/Cu/Pd, Au/Gd, Au/Fe/Cu, Au/Fe/Gd, Au/Fe/Cu/Gd.

73. The nanoparticle according to claim 63, wherein the core is magnetic.

74. The nanoparticle according to claim 63, wherein the core further comprises an NMR active atom selected from the group consisting of: $Mn^{2+}$, $Gd^{3+}$, $Eu^{2+}$, $Cu^{2+}$, $V^{2+}$, $Co^{2+}$, $Ni^{2+}$, $Fe^{2+}$, $Fe^{3+}$ and $lanthanides^{3+}$.

75. The nanoparticle according to claim 63, wherein the core further comprises a semiconductor.

76. The nanoparticle according to claim 75, wherein the semiconductor is selected from the group consisting of: cadmium selenide, cadmium sulphide, cadmium tellurium and zinc sulphide.

77. The nanoparticle according to claim 63, wherein the core comprises a metal oxide coated with a metal selected from the group consisting of: Au, Ag, Cu, Pt, Pd and Zn, or any combination thereof.

78. The nanoparticle according to claim 77, wherein said metal oxide is of the formula $XFe_2O_4$, where X is a metal selected from the group consisting of: Fe, Mn and Co.

79. The nanoparticle according to claim 63, wherein the nanoparticle core has a diameter in the range of about 0.5 nm to about 50 nm.

80. The nanoparticle according to claim 79, wherein said diameter is in the range of about 1 nm to about 10 nm, or is in the range of about 1.5 nm to about 2 nm.

81. The nanoparticle according to claim 63, wherein the nanoparticle comprises a divalent component.

82. The nanoparticle according to claim 81, wherein said divalent component is present in the corona of the nanoparticle.

83. The nanoparticle according to claim 81, wherein said divalent component is selected from the group consisting of divalent metals, divalent metal compounds or other component having a divalent state.

84. The nanoparticle according to claim 81, wherein said divalent component is selected from the group consisting of zinc, magnesium, copper, nickel, cobalt, cadmium, or calcium, and oxides and salts thereof.

85. The nanoparticle according to claim 84, wherein said zinc is selected from: $Zn^{2+}$ and ZnO.

86. The nanoparticle according to claim 85, wherein the zinc comprises $ZnCl_2$.

87. A plurality of nanoparticles as defined in claim 63.

88. The plurality of nanoparticles according to claim 87, wherein the nanoparticle cores have an average diameter in the range of about 0.5 nm to about 50 nm.

89. The plurality of nanoparticles according to claim 88, wherein said average diameter is in the range of about 1 nm to about 10 nm, or is in the range of about 1.5 nm to about 2 nm.

90. A method of stabilising at least one peptide, comprising contacting the at least one peptide with a nanoparticle as defined in claim 63 under conditions which allow the at least one peptide to bind to the corona of the nanoparticle.

91. The method according to claim 90, wherein the at lest one peptide is selected from the group consisting of: insulin, GLP-1, IGF1, IGF2, relaxin, INSL5, INSL6, INSL7, pancreatic polypeptide (PP), peptide tyrosine tyrosine (PTT), neuropeptide Y, oxytocin, vasopressin, GnRH, TRH, CRH, GHRH/somatostatin, FSH, LH, TSH, CGA, prolactin, ClIP, ACTH, MSH, enorphins, lipotropin, GH, calcitonin, PTH, inhibin, relaxin, hCG, HPL, glucagons, insulin, somatostatin, melatonin, thymosin, thmulin, gastrin, ghrelin, thymopoietin, CCK, GIP secretin, motin VIP, enteroglucagon, IGF-1, IGF-2, leptin, adiponectin, resistin Osteocalcin, renin, EPO, calcitrol, ANP, BNP, chemokines, cytokines, adipokines and biologically active analogs thereof.

92. The method according to claim 91, wherein the peptide is monomeric and/or dimeric human insulin.

93. The method according to claim 91, wherein the peptide is GLP-1 or an analogue thereof.

94. The method according to claim 90, wherein the at least one peptide is at least two different species of peptide.

95. The method according to claim 94, wherein the at least two different species of peptide comprise insulin and GLP-1.

* * * * *